(12) United States Patent
Freedman et al.

(10) Patent No.: US 11,994,484 B2
(45) Date of Patent: May 28, 2024

(54) APPARATUS AND METHOD FOR SINGLE CELL DISCRIMINATION

(71) Applicant: The Regents of the University of California, Oakland, CA (US)

(72) Inventors: Kevin Freedman, Lake Elsinore, CA (US); Vinay Sharma, Riverside, CA (US)

(73) Assignee: THE REGENTS OF THE UNIVERSITY OF CALIFORNIA, Oaland (CA)

( * ) Notice: Subject to any disclaimer, the term of this patent is extended or adjusted under 35 U.S.C. 154(b) by 114 days.

(21) Appl. No.: 17/703,783

(22) Filed: Mar. 24, 2022

(65) Prior Publication Data
US 2022/0308001 A1  Sep. 29, 2022

Related U.S. Application Data

(60) Provisional application No. 63/166,122, filed on Mar. 25, 2021.

(51) Int. Cl.
*G01N 27/06* (2006.01)
*G01N 27/447* (2006.01)
(Continued)

(52) U.S. Cl.
CPC ....... *G01N 27/06* (2013.01); *G01N 33/48728* (2013.01); *G01N 11/04* (2013.01); *G01N 27/447* (2013.01)

(58) Field of Classification Search
CPC .......... G01N 9/32; G01N 11/04; G01N 11/06; G01N 11/08; G01N 15/1031;
(Continued)

(56) References Cited

U.S. PATENT DOCUMENTS

| 8,273,532 B2 * | 9/2012 | Gershow | C12Q 1/6825 977/932 |
| 8,980,073 B2 * | 3/2015 | Pourmand | G01Q 60/44 204/403.01 |

(Continued)

FOREIGN PATENT DOCUMENTS

| CA | 2425476 C | * | 2/2011 | ........ | B01J 19/0046 |
| CA | 2864824 A1 | * | 8/2013 | ........ | C12M 47/06 |

(Continued)

OTHER PUBLICATIONS

Varga et al., Size Measurement of Extracellular Vesicles and Synthetic Liposomes: The Impact of the Hydration Shell and the Protein Corona. Colloids and Surfaces B: Biointerfaces 192 (2020) (Year: 2020).*

(Continued)

*Primary Examiner* — Hoai-An D. Nguyen
(74) *Attorney, Agent, or Firm* — Viksnins Harris Padys Malen LLP

(57) ABSTRACT

A method includes providing a fluid to a structure including an aperture, applying a voltage signal to a circuit that includes the fluid, applying a substantially periodic pressure signal to the fluid, detecting a current signal in the circuit as an analyte passes through the aperture in response to the substantially periodic pressure signal, and processing the current signal and the substantially periodic pressure signal to determine a switch time and a release time for the analyte. An apparatus includes a structure including an aperture to receive a fluid, a voltage source to provide a voltage signal to an electronic circuit having a path that includes the aperture, a pressure signal generator to provide a substantially periodic pressure signal to the fluid, and a system to process the periodic pressure signal and a current signal induced in the electronic circuit.

13 Claims, 26 Drawing Sheets

(51) Int. Cl.
*G01N 33/487* (2006.01)
*G01N 11/04* (2006.01)

(58) Field of Classification Search
CPC .... G01N 27/3278; G01N 27/06; G01N 27/12; G01N 33/48721; G01N 27/447; G01N 27/44743; G01N 27/44756; G01N 27/00; G01N 27/02; G01N 27/04; G01N 33/00; G01N 33/48; G01N 33/483; G01N 33/487; G01N 33/48707; G01N 33/48728
USPC .................. 324/71.1, 693, 600, 649, 691
See application file for complete search history.

(56) References Cited

U.S. PATENT DOCUMENTS

| | | | | |
|---|---|---|---|---|
| 9,506,894 | B2* | 11/2016 | Kawai | G01N 27/44752 |
| 9,914,966 | B1* | 3/2018 | Dimitrov | G01N 33/48721 |
| 10,316,355 | B2* | 6/2019 | Mir | C12Q 1/6869 |
| 10,513,434 | B2* | 12/2019 | Seger | G01Q 60/44 |
| 10,612,083 | B2* | 4/2020 | Gundlach | G01N 33/48721 |
| 10,794,895 | B2* | 10/2020 | Xie | B01L 3/50273 |
| 10,913,978 | B2* | 2/2021 | Ivanov | G01N 27/44791 |
| 11,016,053 | B2* | 5/2021 | Huff | G01N 33/54326 |
| 11,243,188 | B2* | 2/2022 | Pourmand | B01L 3/021 |
| 11,499,186 | B2* | 11/2022 | Ju | C07H 19/10 |
| 2009/0136958 | A1* | 5/2009 | Gershow | C12Q 1/6825 977/924 |
| 2012/0222958 | A1* | 9/2012 | Pourmand | G01N 27/3277 977/700 |
| 2012/0225435 | A1* | 9/2012 | Seger | B01L 3/502715 435/7.1 |
| 2014/0183040 | A1* | 7/2014 | Kawai | G01N 27/44752 204/600 |
| 2014/0332381 | A1* | 11/2014 | Siwy | G01N 27/44791 204/451 |
| 2015/0060276 | A1* | 3/2015 | Golovchenko | B01L 3/502761 204/453 |
| 2015/0060277 | A1* | 3/2015 | Golovchenko | G01N 27/44791 204/453 |
| 2016/0231307 | A1* | 8/2016 | Xie | G01N 27/4146 |
| 2017/0211135 | A1* | 7/2017 | Mir | C12Q 1/6825 |
| 2018/0002170 | A1* | 1/2018 | Seger | G01Q 60/44 |
| 2018/0275088 | A1* | 9/2018 | Huff | B01L 3/502761 |
| 2019/0369081 | A1* | 12/2019 | Chen | G01N 33/483 |
| 2020/0024649 | A1* | 1/2020 | Mir | G01Q 60/44 |
| 2020/0400648 | A1* | 12/2020 | Xie | C12Q 1/6869 |
| 2020/0400649 | A1* | 12/2020 | Xie | G01N 33/48721 |
| 2021/0325334 | A1* | 10/2021 | Huff | G01N 33/54326 |
| 2021/0387193 | A1* | 12/2021 | Solomon | G01N 11/04 |
| 2022/0074920 | A1* | 3/2022 | Todd | G01N 27/26 |
| 2022/0236251 | A1* | 7/2022 | Xie | B01L 3/502715 |
| 2022/0277814 | A1* | 9/2022 | Nivala | C12Q 1/682 |
| 2022/0308001 | A1* | 9/2022 | Freedman | G01N 33/48728 |
| 2022/0366313 | A1* | 11/2022 | Gundlach | G01N 33/48721 |
| 2022/0372577 | A1* | 11/2022 | Edel | C12Q 1/6886 |
| 2022/0390347 | A1* | 12/2022 | Platt | G01N 15/1056 |
| 2023/0073771 | A1* | 3/2023 | He | G01N 33/5306 |
| 2023/0220450 | A1* | 7/2023 | Akahori | G01N 27/44791 435/6.11 |
| 2023/0220451 | A1* | 7/2023 | Ivanov | G01N 33/54346 435/6.11 |
| 2023/0256297 | A1* | 8/2023 | Canberk | G02B 27/017 482/8 |

FOREIGN PATENT DOCUMENTS

| | | | | |
|---|---|---|---|---|
| CA | 2909297 | A1 * | 10/2014 | ....... G01N 33/48721 |
| CN | 212688058 | U * | 3/2021 | |
| WO | WO-0118246 | A1 * | 3/2001 | ....... B01L 3/502761 |
| WO | WO-2005074497 | A2 * | 8/2005 | ....... A61K 47/48869 |
| WO | WO-2009045472 | A1 * | 4/2009 | ........... C12Q 1/6825 |
| WO | WO-2011046706 | A1 * | 4/2011 | ............. B82Y 30/00 |
| WO | WO-2012122029 | A2 * | 9/2012 | ............... B01L 3/021 |
| WO | WO-2013123379 | A2 * | 8/2013 | ............ C12M 47/06 |
| WO | WO-2016015018 | A1 * | 1/2016 | ............... B01L 3/021 |
| WO | WO-2016080543 | A1 * | 5/2016 | ........ B01L 3/502715 |
| WO | WO-2018067878 | A1 * | 4/2018 | ........ B01L 3/502715 |
| WO | WO-2019213571 | A1 * | 11/2019 | ........ B01L 3/502707 |
| WO | WO-2020131103 | A1 * | 6/2020 | ............. G01N 27/26 |
| WO | WO-2021079153 | A1 * | 4/2021 | .......... G01N 15/1031 |

OTHER PUBLICATIONS

Akbarzadeh et al. Nanoscale Research Letters 2013, 8:102 http://www.nanoscalereslett.com/content/8/1/102 (Year: 2013).*

Mozafari, M.R., Nanoliposomes: Preparation and Analysis. https://link.springer.com/protocol/10.1007/978-1-60327-360-2_2#Abs1_2 Part of the Methods in Molecular Biology book series (MIMB,vol. 605) (Year: 2009).*

Mehta, Amrita., Loading Nanoliposome Therapeutics Into Red Blood Cells Using Electroporation. Northeastern Univeristy Boston, Massachusetts Jan. 2009 (Year: 2009).*

Jeppesen et al., Extracellular vesicles and nanoparticles: emerging complexities. Trends in Cell Biology, Aug. 2023, vol. 33, No. 8 (Year: 2023).*

Delgado, F , et al., "Intracellular Water Exchange for Measuring the Dry Mass, Water Mass and Changes in Chemical Composition of Living Cells", Plos One 8, e67590, 11 pages (2013).

Gershow, M , et al., "Recapturing and Trapping Single Molecules with a Solid State Nanopore", Nat Nanotechnol 2, 775-779 (2007).

Gorisch, S , et al., "Mobility of multi-subunit complexes in the nucleus: accessibility and dynamics of chromatin subcompartments", Histochemistry and Cell Biology 123, 217-228 (2005).

Grover, W , et al., "Measuring single-cell density", Proceedings of the National Academy of Sciences 108, 10992-10996 (2011).

Hoogerheide, D , et al., "Pressure-Voltage Trap for DNA near a Solid-State Nanopore", ACS Nano 8, 7384-7391 (2014).

Isleib, D , "Density of potato starch", American Potato Journal 35, 428-429 (1958).

Jain, M , et al., "Nanopore sequencing and assembly of a human genome with ultra-long reads", Nat Biotechnol 36, 338-345 (2018).

Lan, W , et al., "Pressure-dependent ion current rectification in conical-shaped glass nanopores", J Am Chem Soc 133, 13300-13303 (2011).

Lan, W , et al., "Pressure-Driven Nanoparticle Transport across Glass Membranes Containing a Conical-Shaped Nanopore", J Phys Chem C 115, 18445-18452 (2011).

Lee, J , et al., "Multiple Consecutive Recapture of Rigid Nanoparticles Using a Solid-state Nanopore Sensor", Electrophoresis 39 (5-6), 833-843 (2018).

Liu, X , et al., "Entropic cages for trapping DNA near a nanopore", Nat Commun 6, 6222, 1-9 (2015).

Luo, L , "Negative Differential Electrolyte Resistance in a Solid-State Nanopore Resulting from Electroosmotic Flow Bistability", ACS Nano 8, 3023-3030 (2014).

Lu, B , et al., "Pressure-controlled motion of single polymers through solid-state nanopores", Nano Lett 13, 3048-3052 (2013).

Noakes, M , et al., "Increasing the accuracy of nanopore DNA sequencing using a time-varying cross membrane voltage", Nat Biotechnol 37, 651-656 (2019).

Panijpan, B , "The buoyant density of DNA and the G + C content", Journal of Chemical Education 54, 172 (1977).

Plesa, C , et al., "Non-equilibrium folding of individual DNA molecules recaptured up to 1000 times in a solid state nanopore", Nanotechnology 24, 475101, 16 pages (2013).

Sharma, R , et al., "Complex DNA knots detected with a nanopore sensor", Nat Commun 10, 4473, 1-9 (2019).

Si, W , et al., "Nanopore Sensing of Protein Folding", ACS Nano 11, 7091-7100 (2017).

Yang, K , et al., "From bead to rod: Comparison of theories by measuring translational drag coefficients of micron-sized magnetic bead-chains in Stokes flow", Plos One 12, e0188015, 18 pages (2017).

(56) References Cited

OTHER PUBLICATIONS

Zhang, H , et al., "Slowing Down DNA Translocation Through Solid-State Nanopores by Pressure", Small 9, 4112-4117 (2013).

* cited by examiner

Capture kinetics for pressure-biased apertures $$\Delta P = 500\sin(2\pi\,10000\,t))$$

$$\Delta P = 500\sin(2\pi t))$$

APPARATUS AND METHOD FOR SINGLE CELL DISCRIMINATION

CROSS REFERENCE TO RELATED APPLICATION

This application claims priority to U.S. Provisional Application No. 63/166,122 filed on 25 Mar. 2021. The entire content of the application referenced above is hereby incorporated by reference herein.

BACKGROUND

Microscale and nanoscale apertures represent a unique class of sensors which provide highly sensitive single-species and multi-species sensing capabilities. Acquiring signals from the translocation of a molecule, or other soft biological matter, principally works by the detection of current changes in a single constricted aperture. Applications include DNA sequencing, sensing of protein folding, and sub-structural analysis. Present methods for detecting analytes suffer from low throughput and other deficiencies described in the disclosure. For these and other reasons there is need for the subject matter of the present disclosure.

SUMMARY

Consistent with the disclosed embodiments, a method for use in detecting an analyte in a fluid is disclosed. The method comprises providing a fluid to a structure including an aperture (e.g., nanopipette or nanopore). The method further comprises applying a voltage signal to a circuit that includes the fluid. The method further comprises applying a substantially periodic pressure signal to the fluid. The method further comprises detecting a current signal in the circuit as an analyte passes through the aperture in response to the substantially periodic pressure signal. And the method further comprises processing the current signal and the substantially periodic pressure signal to determine a switch time and a release time for the analyte.

Consistent with the disclosed embodiments, an apparatus for use in processing a fluid including an analyte is disclosed. The apparatus comprises an aperture (e.g., nanopipette or nanopore) to receive a fluid. The apparatus further comprises a voltage source to provide a voltage signal to an electronic circuit having a path that includes the aperture. The apparatus further comprises a pressure signal generator to provide a substantially periodic pressure signal to the fluid. And the apparatus further comprises a system to process the periodic pressure signal and a current signal induced in the electronic circuit.

The technique described in the invention provides a method for mass-based discrimination in micro and nanoscale objects by rapid acceleration shown on microbial cells. It also enables a method for sorting of micron sized single cells and nanoscale biological entities such as liposomes and vesicles based on size. The size selective pressure reversal can lead to collection of one type of analyte in one fluidic chamber leading to size-based sorting or enriching of the smaller entity on one side of the aperture.

Further, the technique described in the invention enables a method for probing deformation in biological entities such as cells, vesicles, liposomes and other soft biological species by multiple recapture in a nanopore. The analyte can also be exposed to a reactive environment and can be recaptured by pressure reversal and deformation can be probed. In a system where capture and recapture pressure is same, the current drop and dwell time can be used to probe deformation while in case of different pressure, the correction factor can be used as described later on.

Further, the technique described in the invention can make use of multiple parallel apertures to sort or trap individual entities. The size-based sorting can be achieved using an array of apertures and applying pressure conditions as per sorting/trapping requirements. Further, the technique described in the invention can find applications in therapeutics where the cell mass is affected either by pathological conditions or by drug interactions.

BRIEF DESCRIPTION OF THE DRAWINGS

FIG. 2($a$) The experimental setup for pressure-controlled translocation studies. In certain embodiments, the pressure generator and controller are capable of applying desired negative and positive pressure in pressure range of $(-)7 \times 10^5$ Pa to $1 \times 10^6$ Pa. FIG. 2($b$) TEM image of mixed microbial population containing spherical *Micrococcus luteus* and rod shaped *Serratia marcescens* bacterial species. FIG. 2($c$) COMSOL simulations showing flow reversal under negative pressure as well as the fluid velocity during microbial translocation. FIG. 2($d$) SEM image of glass pore used for translocation of microspheres. FIG. 2($e$-$f$) Collapsed image stack of fluorescent microspheres as they are drawn towards the sensor, as well as the fluorescence recording at the tip of the sensor.

FIG. 3($a$) Microchannel with width of 1.6 microns, 1.0 micron particle positioned in the center, and a sinusoidal pressure wave applied to the left side (i.e. inlet). The mean velocity of the fluid (i) and particles of various mass are modelled (ii). FIG. 3($b$) Constricted apertures with the same pressure wave amplitude generated higher velocities which are no longer dependent on pressure wave frequency (i-ii). Since translocations occur on the microsecond timescale, pressure can also adequately be assumed to be constant. FIG. 3($c$) The acceleration of fluid within a constricted aperture (500 mbar) can generate up to 250 k×g which is observed during the deceleration phase (i.e. once the particle exits the aperture). The microchannel with a 500 mbar amplitude pressure wave applied (iii) reaches approximately 800×g of acceleration (peak-to-peak).

FIG. 4($a$) Representative current traces at P=-103 Pa and 700 mV. FIG. 4($b$) Representative current traces at P=97 Pa and 700 mV. FIG. 4($c$) The change in current drop with respect to increasing positive and negative pressure showing a linear drop in 1/ΔI with P. FIG. 4($d$) The change in dwell time with increasing pressure showing an exponential decay in $T_d$ with P. FIG. 4($e$-$f$) The excluded volume without considering the effect of pressure FIG. 4($e$) and the corrected excluded volume FIG. 4($f$) using the same dataset.

FIG. 5($a$) The typical current and pressure signatures for translocation of microspheres. FIG. 5($b$) Translocation event profile for inward and outward microsphere. FIG. 5(c) The correlation between switch time and release time for microsphere recapture. FIG. 5(d) Representative current and pressure signature for bacterial cell translocation. FIG. 5(e) Two distinct "In" and "Out" event signatures for bacterial translocation. FIG. 5(f) The correlation between switch time and release time for two bacterial species translocations under sine pressure wave and constant voltage (600 mV).

FIGS. 6(a-b) Representative current drop signature specific to bacterial species used as template for identification. FIG. 6(c) The current drop distribution for individual bacterial species. FIGS. 6(d-e) Dwell time vs current drop and excluded volume exhibiting two populations FIG. 6(f) Template based identification of individual bacterial species in $T_s$ vs $T_r$ profile of a mixed population under sine pressure wave. FIGS. 6(f)-6(h) The magnitude of applicable forces governs the acceleration and deacceleration of cells leading to identification of different population.

FIG. 7(a) Representative traces of current drop and pressure for capture and release events at a pre-defined switch delay of 500 ms. FIG. 7(b) The distribution of release events at corresponding switch delay time. FIG. 7(c) The recapture probability at different switch and release time showing a 100% recapture if $T_{cutoff} > T_r$. FIG. 7(d) Time-dependent model of the velocity profile in a 250 nm glass nanopipettes with a nanoliposome inside ($\Delta P = 1000$ Pa). FIG. 7(e) Velocity profile of nanoliposome during the initial moments of pressure biasing the pore (1-60 ns). FIG. 7(f) Velocity profile for two nanoliposomes of equal size (160 nm) containing payloads of two different densities (water: 1000 kg/m$^3$ and an arbitrary payload of density 2000 kg/m$^3$). FIG. 7(g) The current and pressure signature for translocation of cell-derived nanoliposomes suspended in 0.1×PBS at 900 mV, ±10 KPa. FIG. 7(h) The switch and release time for individual nanoliposomes under sine pressure wave. FIGS. 7(i-j) The capture triggered release of cell-derived nanoliposomes at a switch delay of ca. 75 ms. Inset: Excluded volume histogram of events with a $T_r$ value in the 75th percentile and above, compared to events with a $T_r$ value in the 25$^{th}$ percentile and below (P-value=0.041).

DESCRIPTION

Figure 1A:
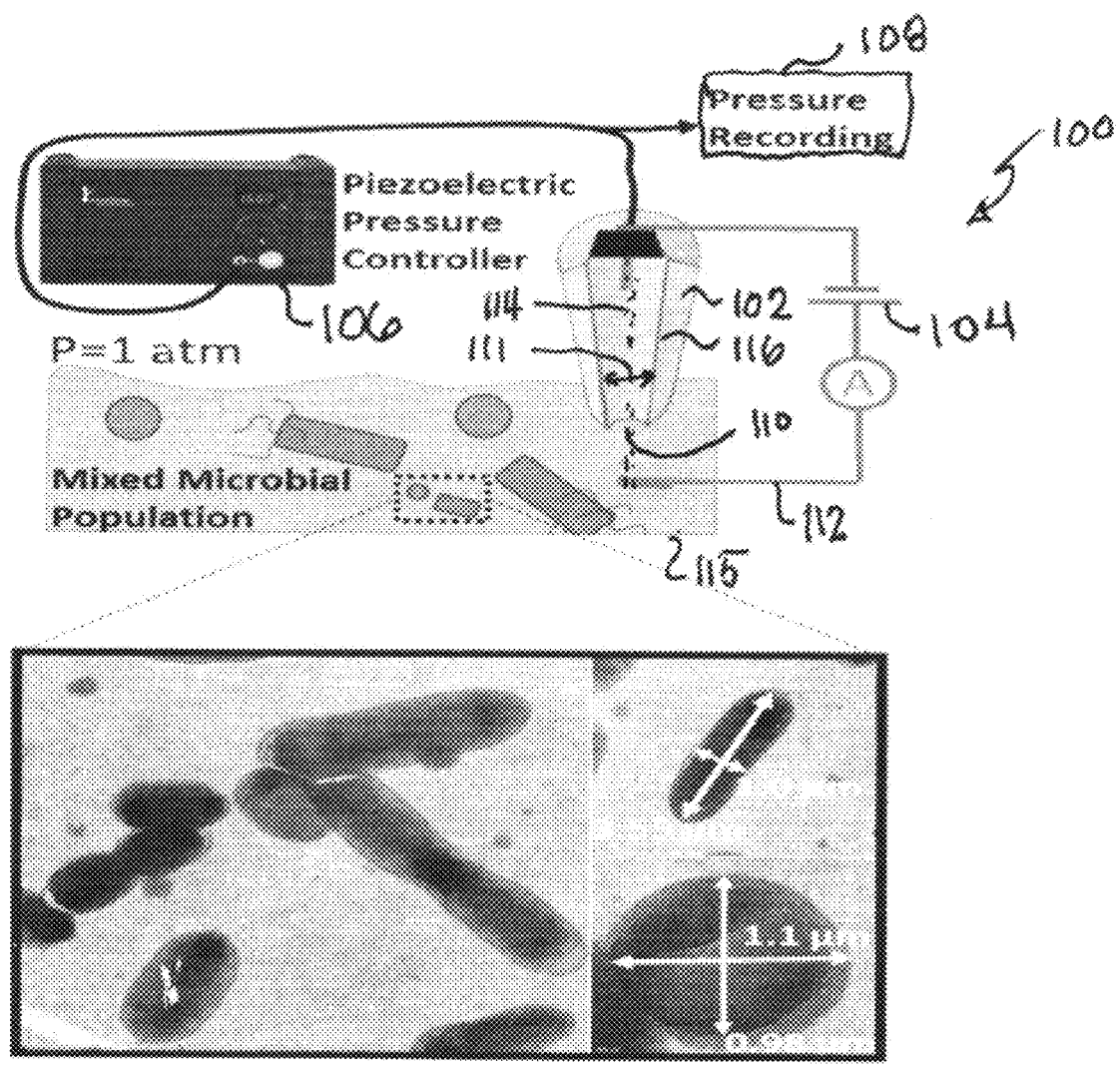
FIG. 1A shows an apparatus including a structure, a voltage source, a pressure signal generator, and a system in accordance with some embodiments of the present disclosure.

FIG. 1A shows an apparatus 100 including a structure 102, a voltage source 104, a pressure signal generator 106, and a system 108 in accordance with some embodiments of the present disclosure. The structure includes an aperture 110 to receive a fluid. The aperture 110 includes a diameter 111. In some embodiments, the diameter 111 has a diameter of between about fifty nanometers and about twenty micrometers. In some embodiments, the diameter 111 is in the nanometer range (e.g., 1 nm to 1000 nm). In some embodiments, the diameter 111 has a diameter of between about 10 nm to 1000 nm. In some embodiments, the diameter 111 has a diameter of between about 50 nm to 1000 nm. In some embodiments, the diameter 111 has a diameter of between about 20 nm to 300 nm. In some embodiments, the diameter 111 has a diameter of between about 30 nm to 250 nm. In some embodiments, the diameter 111 has a diameter of between about 40 nm to 200 nm. In some embodiments, the diameter 111 has a diameter of between about 50 nm to 100 nm. In some embodiments, the diameter 111 has a diameter of between about 1 μm to 100 μm. In some embodiments, the diameter 111 has a diameter of between about 2 μm to 10 μm. In some embodiments, the diameter 111 has a diameter of between about 10 μm to 40 μm. The aperture 110 has a shape and the shape of the aperture 110 is not limited to a particular geometry. In some embodiments, the shape of the aperture 110 is conical. In some embodiments, the shape of the aperture 110 is cylindrical. The aperture 110 can be made of glass, silicon nitride, or any other electrically insulating material. In operation, the voltage source 104 provides a voltage signal to an electronic circuit 112 having a path 114 that includes the aperture 110. The voltage signal is not limited to a particular waveform. In some embodiments, the voltage signal is a direct current signal and has a substantially constant value. In operation, the pressure signal generator provides a substantially periodic pressure signal to the fluid. In operation, the system 108 processes the periodic pressure signal and a current signal induced in the electronic circuit. In some embodiments, the substantially periodic pressure signal includes a positive pressure signal and a negative pressure signal. The structure 102 is not limited to a structure having a particular design. In some embodiments, the structure 102 includes a first chamber 115 and a second chamber 116 in fluid communication through the aperture 110. In operation, the substantially periodic pressure signal produces a pressure differential between the fluid in the first chamber 115 and the second chamber 116.

Figure 1B:
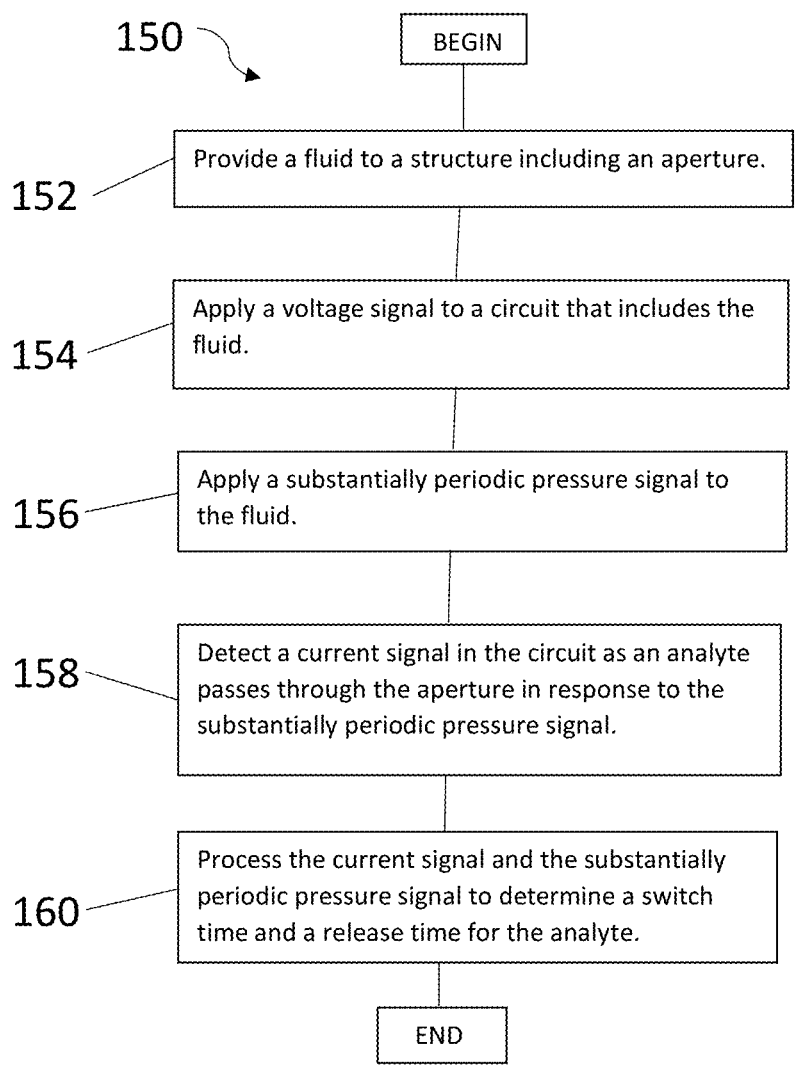
FIG. 1B shows a flow diagram of a method for detecting an analyte in a fluid in accordance with some embodiments of the present disclosure.

FIG. 1B shows a flow diagram of a method 150 for detecting an analyte in a fluid in accordance with some embodiments of the present disclosure. The method 150 includes providing a fluid to a structure including an aperture (block 152), applying a voltage signal to a circuit that includes the fluid (block 154), applying a substantially periodic pressure signal to the fluid (block 156), detecting a current signal in the circuit as an analyte passes through the aperture in response to the substantially periodic pressure signal (block 158), and processing the current signal and the substantially periodic pressure signal to determine a switch time and a release time for the analyte (block 160).

In some embodiments, wherein applying the voltage signal to the circuit that includes the fluid comprises applying a substantially fixed voltage signal to the circuit. In some embodiments, the substantially periodic pressure signal achieves a flow reversal of the fluid. In some embodiments, the substantially periodic pressure signal approximates a sine wave, square wave, or irregular having a peak pressure (positive or negative pressure) of about $1 \times 10^3$ to $1 \times 10^7$ (e.g., $1 \times 10^5$ to $1 \times 10^7$) pascals (e.g., $3 \times 10^3$, $1 \times 10^4$, $5 \times 10^4$, $1 \times 10^5$, $5 \times 10^5$, $1 \times 10^6$, $5 \times 10^6$, $1 \times 10^7$). In some embodiments, the substantially periodic pressure signal approximates a sine wave, square wave, or irregular wave having a peak pressure (positive or negative pressure) of about $3 \times 10^3$ to $1 \times 10^4$ pascals. In some embodiments, the substantially periodic pressure signal approximates a sine wave, square wave, or irregular wave having a peak positive pressure of about $3 \times 10^3$ pascals and a peak negative pressure of about minus $3 \times 10^3$ pascals. In some embodiments, the substantially periodic pressure signal approximates a sine wave, square wave, or irregular wave having a peak pressure (positive or negative pressure) of about $1 \times 10^4$ to $5 \times 10^4$ pascals. In some embodiments, the substantially periodic pressure signal approximates a sine wave, square wave, or irregular wave having a peak positive pressure of about $1 \times 10^4$ pascals and a peak negative pressure of about minus $1 \times 10^4$ pascals. In some embodiments, the substantially periodic pressure signal approximates a sine wave, square wave, or irregular wave having a peak positive pressure of about $5\times10^4$ pascals and a peak negative pressure of about minus $5\times10^4$ pascals. In some embodiments, the substantially periodic pressure signal approximates a sine wave, square wave, or irregular wave having a peak positive pressure of about $1\times10^6$ pascals and a peak negative pressure of about minus $7\times10^5$ pascals. In some embodiments, higher pressures may generate higher gradients and/or accelerations, therefore more sensitive signal resolving (e.g., mass resolving). In some embodiments, the substantially periodic pressure signal approximates a sine wave, square wave, or irregular wave having a peak positive pressure of about $1\times10^7$ pascals and a peak negative pressure of about minus $1\times10^7$ pascals. In some embodiments, applying a substantially periodic pressure signal to the fluid comprises tuning the substantially periodic pressure signal to pass the analyte through of the aperture more than once. In some embodiments detecting a current signal in the circuit as an analyte passes through the aperture in response to the substantially periodic pressure signal comprises detecting the current signal in the circuit as a plurality of different biological species pass through the aperture. In some embodiments, processing the current signal comprises analyzing a current drop of the current signal and a dwell time of the current signal to determine a characteristic of the analyte. In some embodiments, the fluid includes one or more bacterial species.

In some embodiments, the method 150 further includes analyzing the switch time and the release time to determine one or more characteristics of the analyte. In some embodiments, the method 150 further includes analyzing the switch time and the release time to determine a physical property of the analyte. In some embodiments, the method 150 further includes processing the switch time and the release time to determine one or more characteristics of the analyte. In some embodiments, the aperture has a diameter of about 250 nanometers and the analyte includes a red blood cell-derived nanoliposome. In some embodiments, the aperture has a diameter of about 250 nanometers and the analyte includes an empty and/or drug-loaded nanoliposome. In some embodiments, the method 150 further includes triggering a change in polarity of the pressure signal upon inward translocation of the analyte. In some embodiments, the analyte is oscillated multiple times across the aperture to obtain an averaged measurement or characteristic (e.g., acceleration, mass, mass/charge ratio, size and/or volume) of the analyte.

The subject matter of the disclosure relates to the resistive pulse sensing technology. This disclosure provides a method for discriminating different population of cells using recapture of single cells in the nanopore. This technology discriminates cells on the basis of mass, size and/or volume. The strategy used for the discrimination is acceleration and deacceleration of cells when recaptured in a nanopore using pressure polarity reversal. The direction of pressure governs the direction of cells under an applied voltage bias. Under an applied negative or positive pressure, single cell is captured or released, the corresponding current signals are recorded. The relation between capture time and release time is used to distinguish cells on the basis of their mass, size and/or volume. The lag time between initiation of flow and acceleration of cells leads to differentiation of cells on the basis of mass, size and/or volume as reflected in capture time vs release time plot. The method is useful because it is based on electrical measurements instead of optical measurements as in case of flow cytometer. The present method overcomes the need of fluorescence staining of cells and can operate on a size range of nanometer to micrometers. This method overcomes the limitation of existing fluorescence-based cell discrimination since no fluorescence labelling of cells is required. This technique offers a way of analyzing cells in their native state and discriminate on the basis of mass, size and/or volume.

The disclosure provides for the discrimination of an analyte including cells and particles in solid-state nanopores. The developed method performs the recapture of the analyte by reversing the direction of pressure, keeping the voltage polarity same. A mixture of two bacterial species is translocated and recaptured. The described technique establishes pressure assisted recapture as an advanced cell discrimination method overcoming the limitation of flow cytometer.

In certain embodiments, the analyte is a cell. In certain embodiments, the analyte is a bacteria cell or fungus cell (e.g., yeast). In certain embodiments, the analyte is a virus (e.g., live or inactivated virus). In certain embodiments, the analyte is a virus-like particle. In certain embodiments, the analyte is a particle (e.g., microparticle or nanoparticle). In certain embodiments, the particle is a spherical or rod particle. In certain embodiments, the analyte is a magnetic particle (e.g., paramagnetic particle). In certain embodiments, the analyte is a metal particle (e.g., gold or silver particle). In certain embodiments, the analyte is a polymeric particle (e.g., PLGA or PLA). In certain embodiments, the analyte is a nanorod or nanotube (e.g., carbon nanotube). In certain embodiments, the analyte is a liposome (e.g., empty nanoliposome or drug loaded nanoliposome). In certain embodiments, the analyte is a micelle. In certain embodiments, the analyte is an extracellular vesicle (e.g., exosome).

In certain embodiment, the fluid is saline (e.g., 0.9% Sodium Chloride, phosphate buffer saline, or Ringer's lactate solution) or diluted saline (e.g., 0.1×PBS).

In certain embodiments, the structure including an aperture is a pipette tip (e.g., micropipette or nanopipette). In certain embodiments, the structure including an aperture is a hollow microneedle (e.g., micron or submicron internal diameter hollow microneedle). In certain embodiments, the structure including an aperture is a solid-state film, membrane or wall including an aperture. For example, the solid-state film, membrane or wall separate a first chamber and a second chamber, wherein the first chamber and the second chamber are in fluid communication through the aperture.

In certain embodiments, the structure including an aperture comprises silicon-based material (e.g., silicon nitride or silicon oxide). In certain embodiments, the structure including an aperture comprises glass (e.g., borosilicate). In certain embodiments, the structure including an aperture comprises polymeric material (e.g., polycarbonate, poly (methyl methacrylate), polystyrene). In certain embodiments, the structure including an aperture comprises metal or metal oxide material (e.g., aluminum oxide). In certain embodiments, the structure including an aperture comprises ceramic material. Methods and materials known in fabricating pipette tip, hollow microneedle, or microfluidics chip may be used for producing the structure including an aperture described herein.

In certain embodiment, the method or apparatus described herein may be used for single analyte (e.g., single cell, single particle) characterization (e.g., mass, mass/charge ratio, size, volume, density, and/or morphology). In certain embodiment, the method or apparatus described herein may be used for analyte population discrimination, characterization or clustering analysis for a fluid that comprises one or more analyte(s). In certain embodiments, the fluid comprises one or more population of cells or particles, or mixture thereof. In certain embodiment, the method or apparatus described herein may be used for assessing drug loading and/or release from an analyte (e.g., drug-loaded liposome, particle or micelle).

In certain embodiment, the method or apparatus described herein may be used for endpoint or in-line sensing, measurement or quality control for manufacturing of an analyte. For example, the method or apparatus described herein may be integrated with manufacturing line or processes (e.g., a bioreactor or a reaction container) to monitor the manufacturing of an analyte (e.g., particles, micelle, liposome or virus). In certain embodiments, the method or apparatus described herein may be used to provide real-time in-line sensing for continuous manufacturing of an analyte without disrupting manufacturing and may eliminate invasive aliquot sampling or risk of sampling contamination.

Certain non-limiting, exemplary embodiments of the invention are described as follows.

Embodiment 1. A method comprising:
providing a fluid to a structure including an aperture, nanopipette, or nanopore;
applying a voltage signal to a circuit that includes the fluid containing analyte;
applying a substantially periodic pressure signal to the fluid; and
detecting a current signal in the circuit as an analyte passes through the aperture in response to the substantially periodic pressure signal.

Embodiment 2. The method of embodiment 1, further comprises processing the current signal and the substantially periodic pressure signal to determine timing properties, such as the switch time and a release time for the analyte.

Embodiment 3. The method of embodiment 1, wherein applying the voltage signal to the circuit that includes the fluid comprises applying a substantially fixed voltage signal to the circuit.

Embodiment 4. The method of embodiment 1, wherein the substantially periodic pressure signal achieves a flow reversal of the fluid.

Embodiment 5. The method of embodiment 1, wherein the substantially periodic pressure signal approximates a sine wave, square wave, or irregular wave having a peak positive pressure of about $10\times10^6$ pascals and a peak negative pressure of about minus $10\times10^6$ pascals.

Embodiment 6. The method of embodiment 1, wherein applying a substantially periodic pressure signal to the fluid comprises tuning the substantially periodic pressure signal to pass the analyte through of the aperture more than once.

Embodiment 7. The method of embodiment 1, wherein detecting a current signal in the circuit as an analyte passes through the aperture in response to the substantially periodic pressure signal comprises detecting the current signal in the circuit as a plurality of different biological species pass through the aperture.

Embodiment 8. The method of embodiment 2, wherein processing the current signal comprises analyzing a current drop of the current signal and a dwell time of the current signal to determine a characteristic of the analyte.

Embodiment 9. The method of embodiment 1, wherein the fluid includes one or more bacterial species.

Embodiment 10. The method of embodiment 1, wherein the fluid includes nanoliposomes or extracellular vesicles.

Embodiment 11. The method of embodiment 1, wherein the fluid includes mammalian cells.

Embodiment 12. The method of embodiment 2, further comprising analyzing the switch time and the release time to determine one or more characteristics of the analyte.

Embodiment 13. The method of embodiment 2, further comprising analyzing the switch time and the release time to determine a physical property of the analyte.

Embodiment 14. The method of embodiment 2, further comprising processing the switch time and the release time to determine one or more characteristics of the analyte.

Embodiment 15. The method of embodiment 1, wherein the aperture has a diameter of 50-1000 nanometers and the analyte includes a red blood cell-derived nanoliposome.

Embodiment 16. The method of embodiment 1, further comprising triggering a change in polarity of the pressure signal upon inward translocation of the analyte.

Embodiment 17. The method of embodiment 1, where the current drop is corrected w.r.t. the pressure.

Embodiment 18. The method of embodiment 1, where the aperture contains a reactive environment to react with the analyte.

Embodiment 19. The method of embodiment 1, where analyte is a soft biological entity.

Embodiment 20. The method of embodiment 1, where biological deformation is probed.

Embodiment 21. The method of embodiment 1, where drug loading on nanoliposome is probed.

Embodiment 22. The method of embodiment 1, where cell mass is probed as an indicator of pathological condition of cell.

Embodiment 23. The method of embodiment 1, where cell mass is probed to study the drug interaction with cell.

Embodiment 24. The method of embodiment 1, where percentage or type of different analytes in a mixed population is probed.

Embodiment 25. The method of embodiment 1, where drug loading efficiency of liposome, cells, or biomolecules is probed.

Embodiment 26. The method of embodiment 1, where the fluidic chamber contains different fluids.

Embodiment 27. The method of embodiment 1, where size based sorting is performed on analytes.

Embodiment 28. An apparatus comprising:
a structure including an aperture (nanopipette or nanopore) to receive a fluid;
a voltage source to provide a voltage signal to an electronic circuit having a path that includes the aperture;
a pressure signal generator to provide a substantially periodic pressure signal to the fluid; and
a system to process the periodic pressure signal and a current signal induced in the electronic circuit.

Embodiment 29. The apparatus of embodiment 28, wherein the structure includes a first chamber and a second chamber in fluid communication through the aperture.

Embodiment 30. The apparatus of embodiment 29, wherein the substantially periodic pressure signal to produce a pressure differential between the fluid in the first chamber and the second chamber.

Embodiment 31. The apparatus of embodiment 28, wherein the substantially periodic pressure signal includes a positive pressure signal and a negative pressure signal.

Embodiment 32. The apparatus of embodiment 31, wherein the voltage signal has a substantially constant value.

Embodiment 33. The apparatus of embodiment 32, wherein the aperture has a diameter of between about one-half micrometer and about three micrometers.

Embodiment 34. The apparatus of embodiment 33, wherein the aperture has a substantially conical shape.

Embodiment 35. The apparatus of embodiment 28, where multiple parallel apertures (array of nano or micro pores) are used.

The invention will now be illustrated by the following non-limiting Example.

Example 1

Summary

A single molecule and single cell sensing via the passage through a constricted aperture is a powerful and robust technology which is being utilized broadly; from DNA sequencing to single virus and cell characterization. Micro and nanoscale structures typically translocate a constricted aperture, or pore, using electrophoretic force. In the present disclosure, pressure-induced flow is shown to dominate over electrophoretic and electroosmotic flows yielding a robust sensing platform for a mixed population of microbial species as well as cell-derived nanoliposomes. Unexpectedly, the rapid acceleration of microscale and nanoscale structures also can achieve mass discrimination for individual translocating entities. Described herein is this mass-sensing phenomenon as well as other features of pressure controlled sensing within constricted apertures. The methods described improve the accuracy of single cell and single liposome and vesicle sizing and identification for diagnostic and bioanalytical applications.

Introduction

Slowing down the translocation speed of molecules has been particularly challenging area of research. Among the strategies that have been employed include the application of pressure to nanoscale solid-state pores. Due to the extremely high hydrodynamic resistance associated with nanoscale pores ($10^{21}$ kg m$^{-4}$s$^{-1}$), pressure is unlikely to be the dominant translocation mechanism. Despite the challenges associated with applying large pressure gradients, there are clear advantages associated with pressure being the dominant translocation mechanism, including (1) having the speed of translocation uncoupled from the electrical sensing mechanism, (2) the same biological entity can be captured and recaptured using pressure alone, and (3) the reversibility of viscous-dominated flow could yield 100% recapturing efficiency.

An additional challenge of pressure-induced flow within constricted apertures is the ability to discriminate biological structures according to mass. In a typical sensing experiment, a voltage bias is applied which is nearly entirely consumed by the high resistance of the aperture. Analogously, hydrodynamic resistance is maximum inside the aperture. Therefore, the pressure-induced flow reaches its maximum within the confines of the constricted aperture. For a tapered aperture with internal diameter of 1.6 microns and a moderate pressure bias of 500 mbar, flow velocities are expected to exceed 2 m/s. Assuming a biological structure transits the pore within 100 microseconds, the structure would accelerate from approximately 0 m/s to 2 m/s reaching accelerations of >2,000 times that of Earth's gravity. By assuming initially zero velocity, acceleration may be overestimated however assuming the acceleration is constant (i.e. linearly increasing velocity) most likely greatly underestimates the acceleration (particles are expected to exponentially increase their velocity as they approach the constricted aperture). The large accelerations generated within the aperture create an inertial field defined as the second time derivative of space. Furthermore, a particle's response to the field is governed by Newton's Second Law of Motion, which is mass-dependent. The same principle is commonly used to describe the mass-sensing mechanisms of a quartz crystal microbalance. The 5 MHz oscillations on the surface of the quartz electrode typically generate 5 million g's of acceleration. The frequency of the oscillations become damped as the extremely small masses of biological species absorb to the surface. Constricted apertures make up a previously unknown inertial mass sensor.

The general framework proposed is that pressure can be used as the driving force for translocations as well as generating an inertial field locally at the tip of micro and nanoscale tips. In order to capture mass information, a mechanism must be in place to sense the structure's movement in space at two locations or, alternatively, the biological structure itself can be oscillated within a single sensor and the time interval between events should correlate with the structure's mass. This framework also addresses a general concern with single cell and single molecule measurements which is that only one measurement per entity has some degree of noise/variation that hinders measurement fidelity. Assuming the biological structure is not changing pre-translocation and post-translocation, the error associated with a single measurement can be reduced. If the biological structure is changing pre-translocation and post-translocation, the repeated measurement of the biological structure also offers the possibility to study the chemical or biomechanical transformations which may occur in solution.

The strategies used for single molecule recapture so far are primarily limited to voltage reversal which leads to a change in the direction of electrophoretic force. However, a drawback of the voltage polarity reversal is the large current spikes due to the charging/capacitance effect which are observed to last around 100 ms. One potential issue arising from membrane capacitance is that no event can be recorded in this time period which potentially limits the success of detecting the recapture events.

Up until now, pressure has primarily been used to add an additional force to a translocating molecule in the hopes of slowing down the translocation speed. Drag force on the molecule opposed the electrophoretic force and permitted resolving smaller DNA molecules than previously shown possible. A balance of pressure driven viscous flow and electrophoretic force was used to demonstrate a DNA trap near the nanopore. The change in event frequency has previously been studied with application of pressure. However, the use of pressure has also been shown to effect essential Voltage-Current characteristics of the sensor through the disruption of the ionic distribution near the pore. However, a detailed analysis of the impact of pressure on event characteristics has not been explored to date. This disclosure elucidates the effects of pressure on the recorded signals and derive methods to obtain physically relevant properties of the translocating species such as size and volume. By obtaining mass and volume information, density can perhaps be calculated.

This disclosure describes the impact of pressure on the event characteristics of micro and nanoscale biological entities including (1) bacteria, (2) red blood cell (RBC)-derived nanoliposomes, and (3) empty or drug-loaded nanoliposome. RBC nanoliposomes are a promising drug delivery construct which makes use of a patient's own lipids and thereby extends the lifetime of the nanoliposomes in the patient. For each of these biological structures, solid-state beads are used for calibration. Further, a method is developed to recapture single cell by reversing the direction of pressure, keeping the voltage polarity constant throughout the process. A mixture of two bacterial species are translocated and recaptured, each distinctly differentiated by ionic current as well as their recapture dynamics. To further control the recapture process, event triggered recapturing is developed for the precise timing of the recapture events. Despite the higher hydrodynamic resistance, pressure-controlled recapturing of single nanoscale particles is also accomplished on RBC nanoliposomes. The reported technique establishes pressure-controlled recapture mechanism as a method to yield mass and pressure-corrected volume measurements for the first time.

Results

Figures 2A, 2B, 2C:
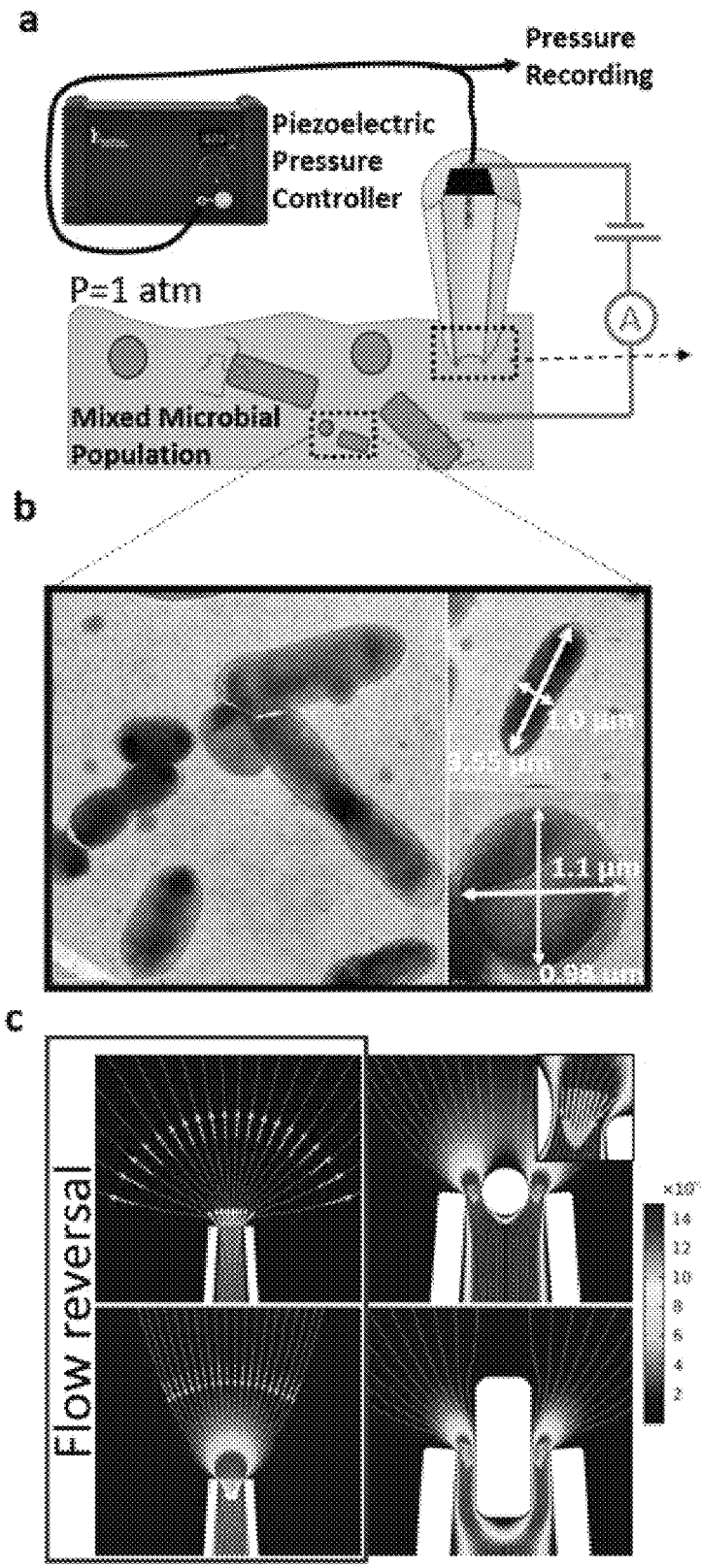
FIGS. 2A-2F.
Figures 2D, 2E, 2F:
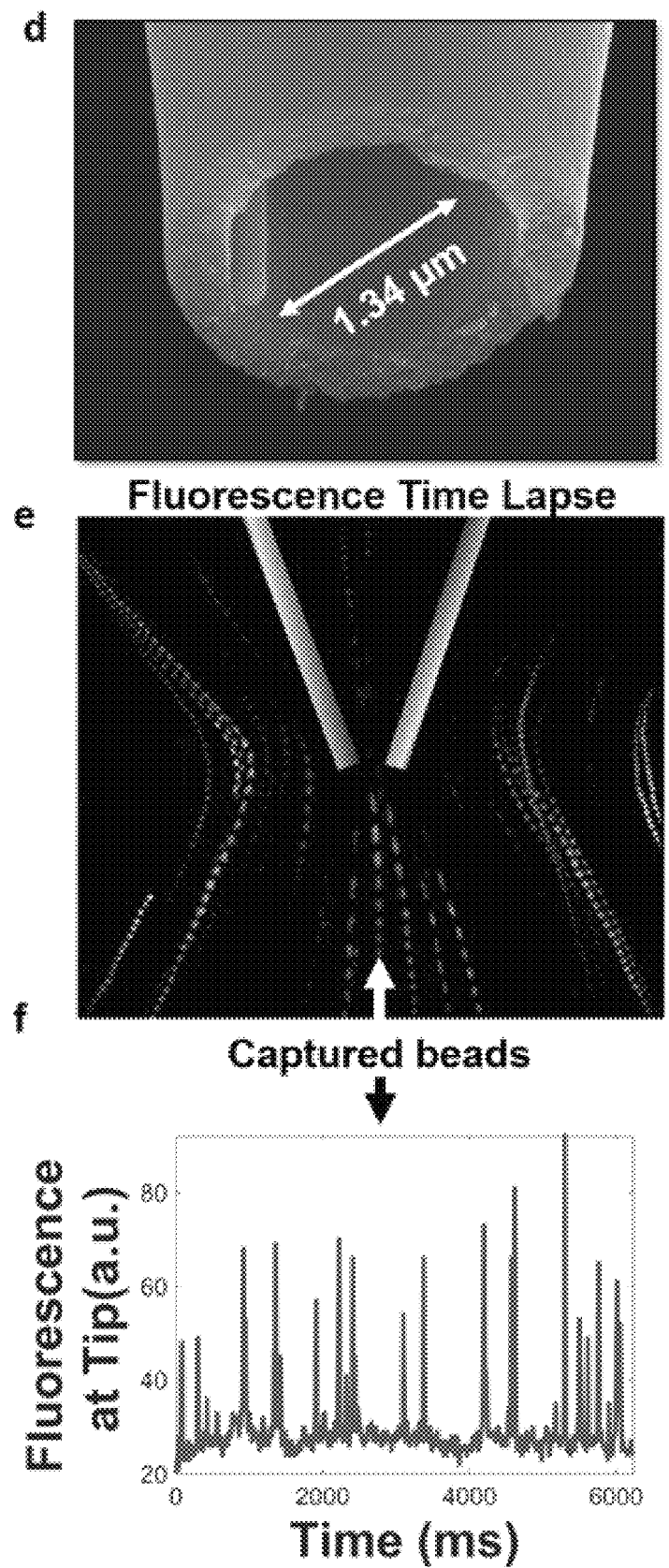
Figure 5A:
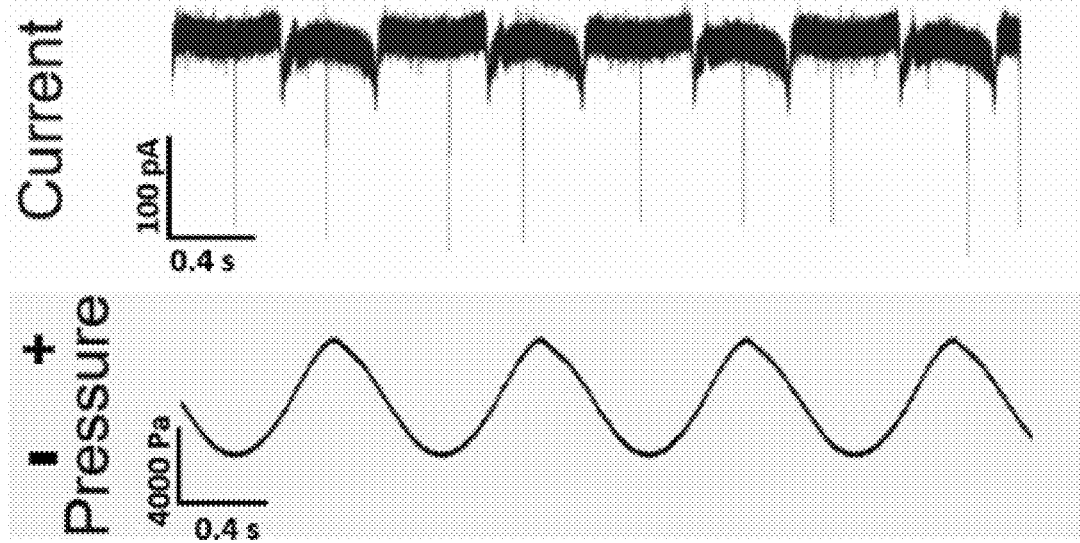
FIGS. 5A-5F. Pressure-controlled recapture of microsphere and bacterial cells.
Figure 5B:
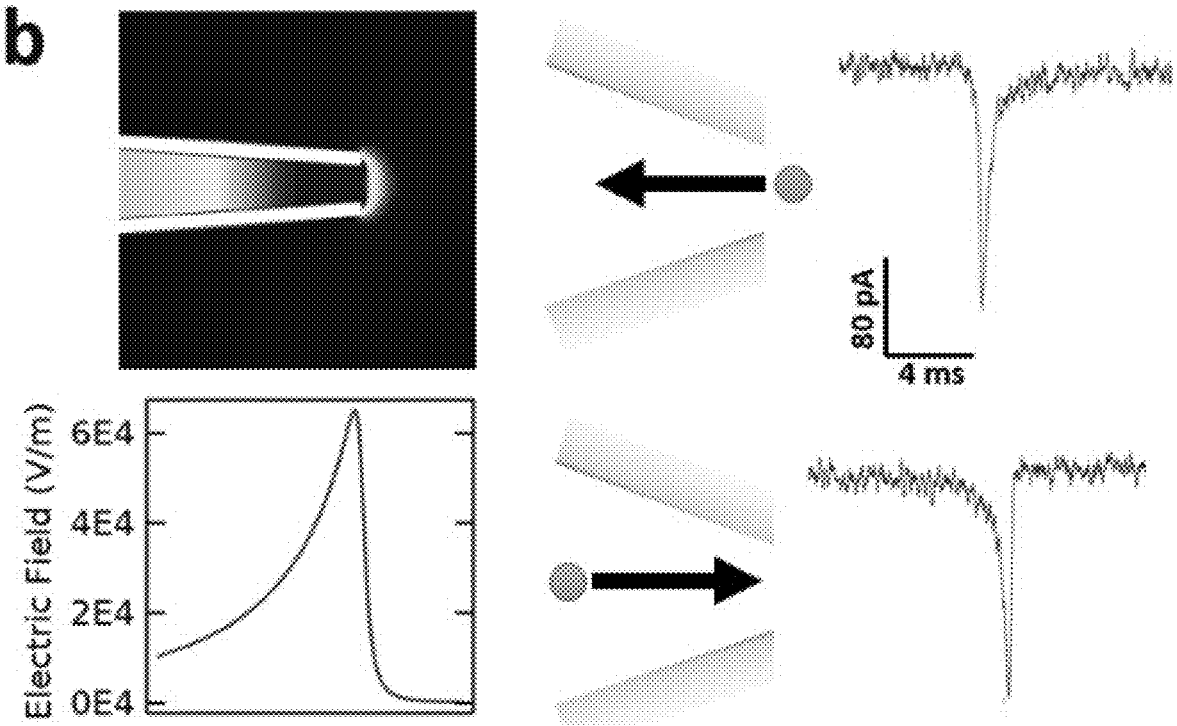

Utilizing pressure as a tool to overcome electroosmotic flow and electrophoretic force was achieved using a custom-built flow chamber made to accommodate pressure control, pressure recording, and ionic current recording (see, FIG. 5a showing a piezoelectric pressure controller connected to a solid state nanopore). While constricted aperture sensing typically relies on an electrophoretic force as the means for inducing translocations events, electroosmotic flow can act to either facilitate or block translocation events as well. In particular, glass apertures with a low salt filling solution are capable of electroosmotic-dominant transport stemming from the accumulation of counterions at the negatively-charged glass surface. Indeed, for borosilicate pores (1-2 µm), positive voltage applied inside the pipette (0-1000 mV), and 0.1×PBS filling solution, electroomostic flow was directed outwards (i.e. inside of the glass pipette to outside the glass pipette). Translocations attempts of carboxylate modified polystyrene microspheres (mean diameter of 1 µm) where unsuccessful under all applied voltages. Numerical methods confirmed a net outward flow at 600 mV voltage and 0 Pa pressure. Negative pressure was applied which shows a flow reversal at ~180 Pa of negative pressure and net inward flow is thus observed (FIG. 2c). Using fluorescent microspheres, the flow field generated by the negative pressure was also studied experimentally. It was found that the capture volume is not spherical or hemispherical like in electrophoretic capture, but rather conical (FIG. 2e). By integrating the intensity acquired around a region of interest around the pipette tip, a time trace of fluorescence was acquired with pulses of fluorescence corresponding to translocation events (FIG. 2f).

Figure 3A:
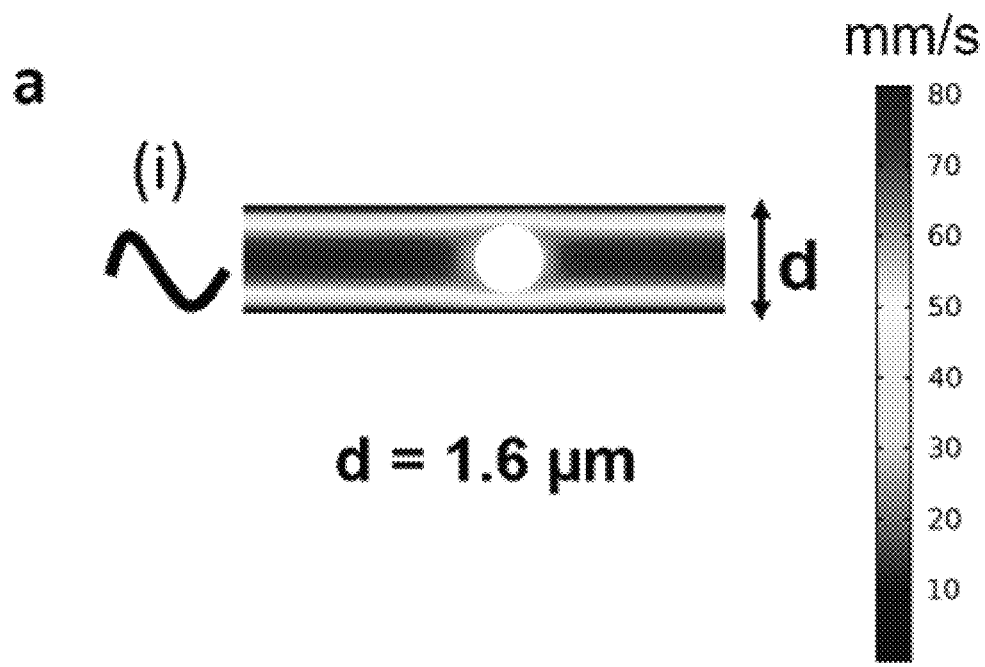
FIGS. 3A-3C. Velocity and acceleration profiles for sinusoidal pressure waves.
Figure 3A:
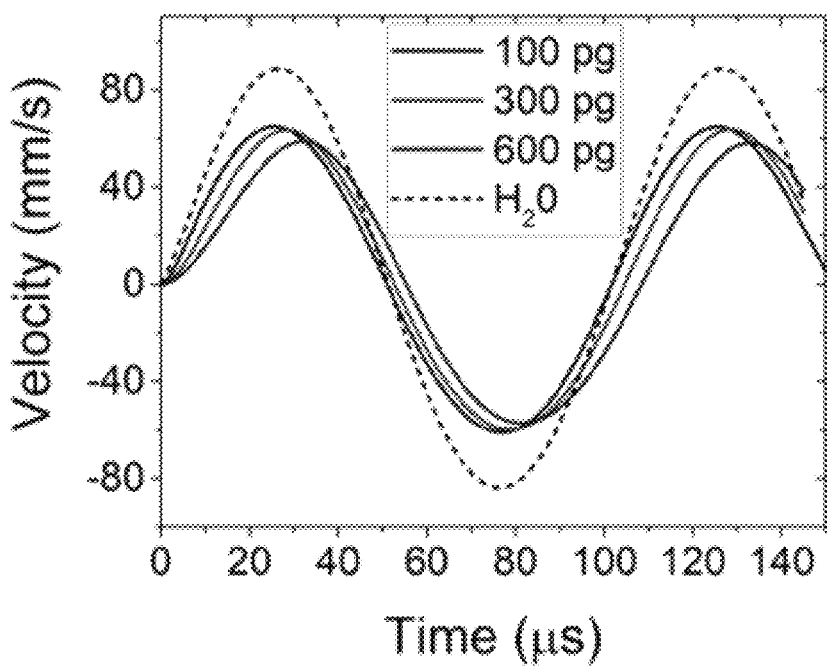
Figure 3B:
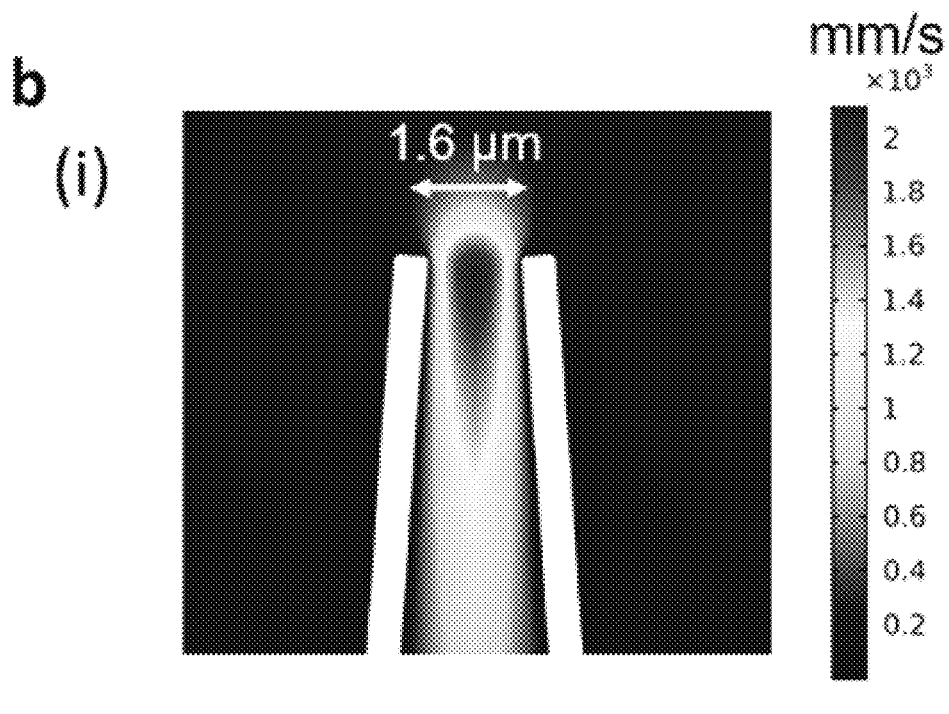
Figure 3B:
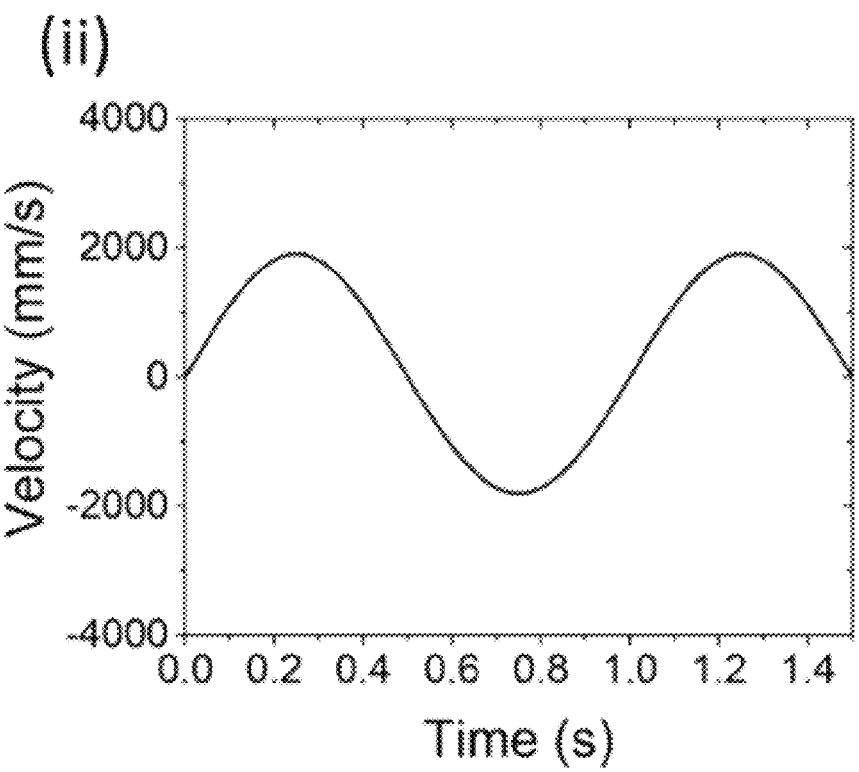

A comparative numerical study of pressure-biased microchannels and constricted apertures was utilized to investigate the velocity and acceleration gradients experienced by translocating structures. Similar 1.6 µm feature sizes were used for building the model and a sinusoidal pressure was applied through an inlet. For the microchannel, the velocity magnitude is a function of the peak pressure, however the acceleration of the particle is strictly linked to the frequency of the pressure wave. In order to accelerate the particle to the maximum velocity within a short period of time, frequencies as high as 10000 Hz were modelled. It is important to note that the pressure wave frequencies of >2 Hz are not achievable in practice due to time associated with pressurizing and evacuating the volume of space upstream from the aperture's filled reservoir. Nevertheless, oscillations of the particle were observed and shown to be mass-dependent (FIG. 3a). Mass produced a lag between fluid velocity and particle velocity. In all cases, the particle's size was kept constant and thereby the drag force on the particle exerted by the passing fluid was also the same for all simulations. For constricted apertures, ΔP is concentrated to the orifice of the aperture and generates much higher fluid velocities (FIG. 3b). Perhaps most importantly, since the translocation process is typically <1 ms, the transient occupancy of the aperture itself is sufficient to accelerate and decelerate the particle within a small window of time.

Figure 3C:
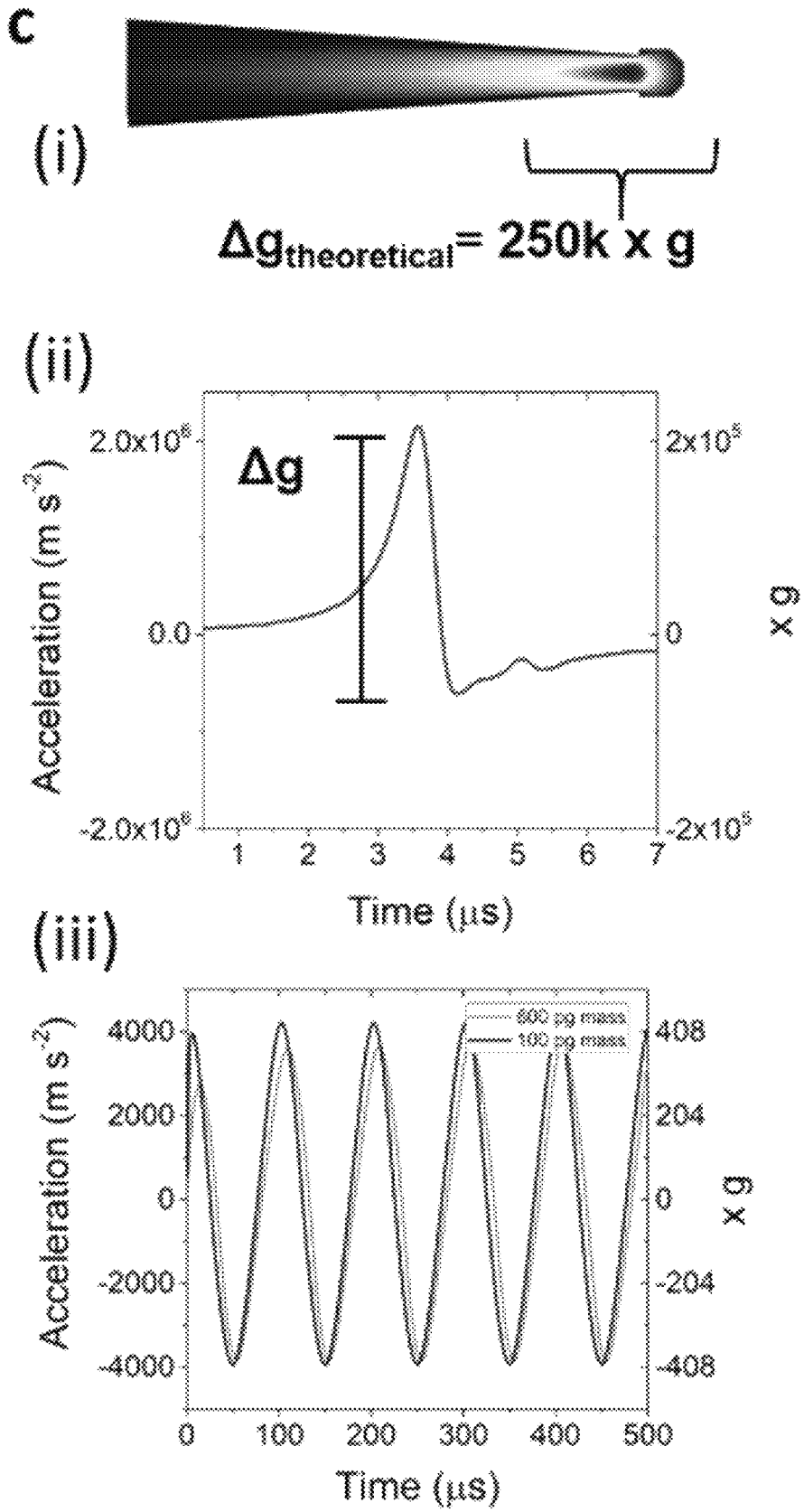

The rapid speed at which particles flow through the aperture is critical for generating the transient spike in acceleration which particles respond to in a mass-dependent fashion. By plotting the acceleration of the fluid as a function of time, we can obtain an upper limit for the accelerations that are possible for the particles. Due to the asymmetric geometry of the apertures (cp. FIG. 2d), the greatest change in acceleration occurs once the particle leaves the pipette and undergoes a rapid deceleration process, producing up to Δg of 250 k×g for a moderate pressure amplitude of 500 mbar (FIG. 3c(i)-(ii)). Within the microchannel, a Δg of 800×g is observed (peak-to-peak; FIG. 3c(iii)). The acceleration of 250 k×g, however, is theoretical and represents the acceleration of a mass-less object. Experimentally, the translocating entity never reaches the peak velocity of 2 m/s due to the velocity of the translocating object lagging the velocity of the fluid. This can be clearly observed by the extremely short timescale of FIG. 3c.

1. Effect of Pressure on Current Blockades

At a low negative pressure (≈-200 Pa), the translocation of polystyrene microspheres was experimentally observed from the cis chamber (i.e. outside the pipette) to trans chamber (i.e. inside the pipette). Interestingly, after microspheres were translocated into the pores, applying a positive pressure reverses the translocation of polystyrene microspheres from trans chamber to cis chamber at +700 mV (FIG. 4(a-b)). An event was classified as a transient drop in current caused by a polystyrene microsphere passing through the pore. To assess the impact of pressure on event characteristics, the translocation of polystyrene microspheres was studied at various negative and positive pressure keeping the voltage constant at +700 mV. The current drop and dwell time for all events were extracted using a custom MATLAB script where the current drop higher than at least 10 standard deviation of baseline current was analyzed. In order to precisely study the impact of pressure on the event characteristics, all doublet events (i.e. aggregates) were disregarded which were ~9% of all events studied. Any application of pressure (i.e. deviation from atmospheric) resulted in a decrease in both the current drop and the dwell time. The median current drop at 700 mV reduced from 0.811±0.09 nA at 0 Pa to 0.286±0.05 nA at 6900 Pa. At a higher negative pressure of -8000 Pa, the median current drop was obtained to be 0.272±0.04 nA. The change in current drop and dwell time at different pressure is shown in FIG. 4(c-d). The curve that best fits the influence of pressure on current drop is an inversely proportional function leading to pressure causing a linear drop in $1/\Delta I$. The best fitting function for dwell time, was an exponential, leading to the decay of dwell time as pressure deviates from atmospheric. The median dwell time at 700 mV reduced from 0.668±0.08 ms at 0 Pa to 0.088±0.010 ms at 6900 Pa. At an almost similar negative pressure of -6890 Pa, the median dwell time is 0.10±0.018 ms. Although pressure is the dominant force in these experiments, we do expect some influence of electroosmostic flow (EOF) on the pressure-driven flow velocity. The slightly longer dwell time of the inward events (against EOF) as compared to the outward events (with EOF) is expected given that EOF adds to or reduces the pressure-induced flow velocity. Using COMSOL, it was found that the fluid velocity at +1000 Pa and −1000 Pa led to slightly different mean fluid velocities of 19.55 mm/s (with EOF) and 15.74 mm/s (against EOF), respectively.

Figures 4A, 4B, 4C:
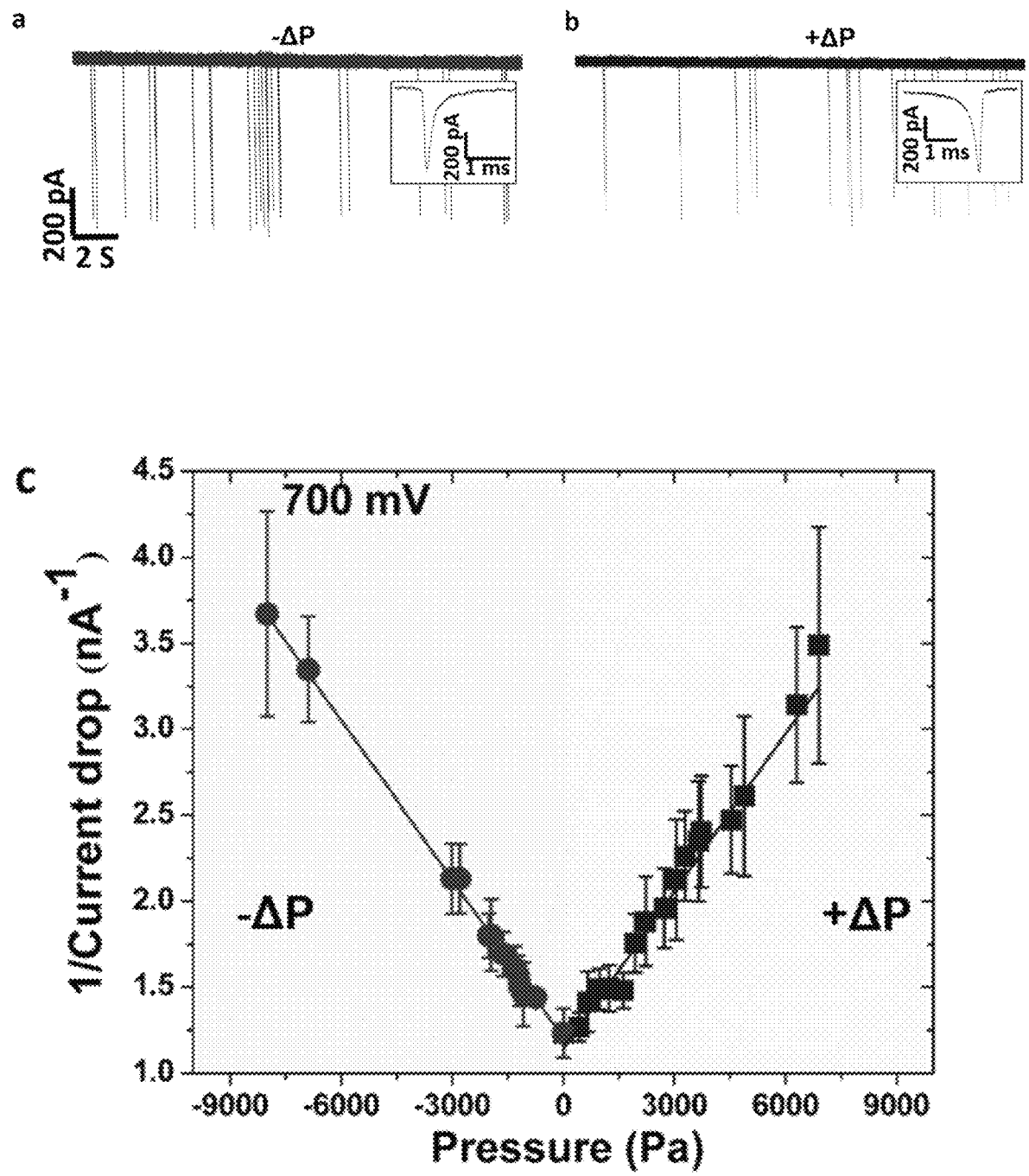
FIGS. 4A-4F. Effect of pressure on translocation dynamics of polystyrene microsphere in a glass nanopore.
Figure 4D:
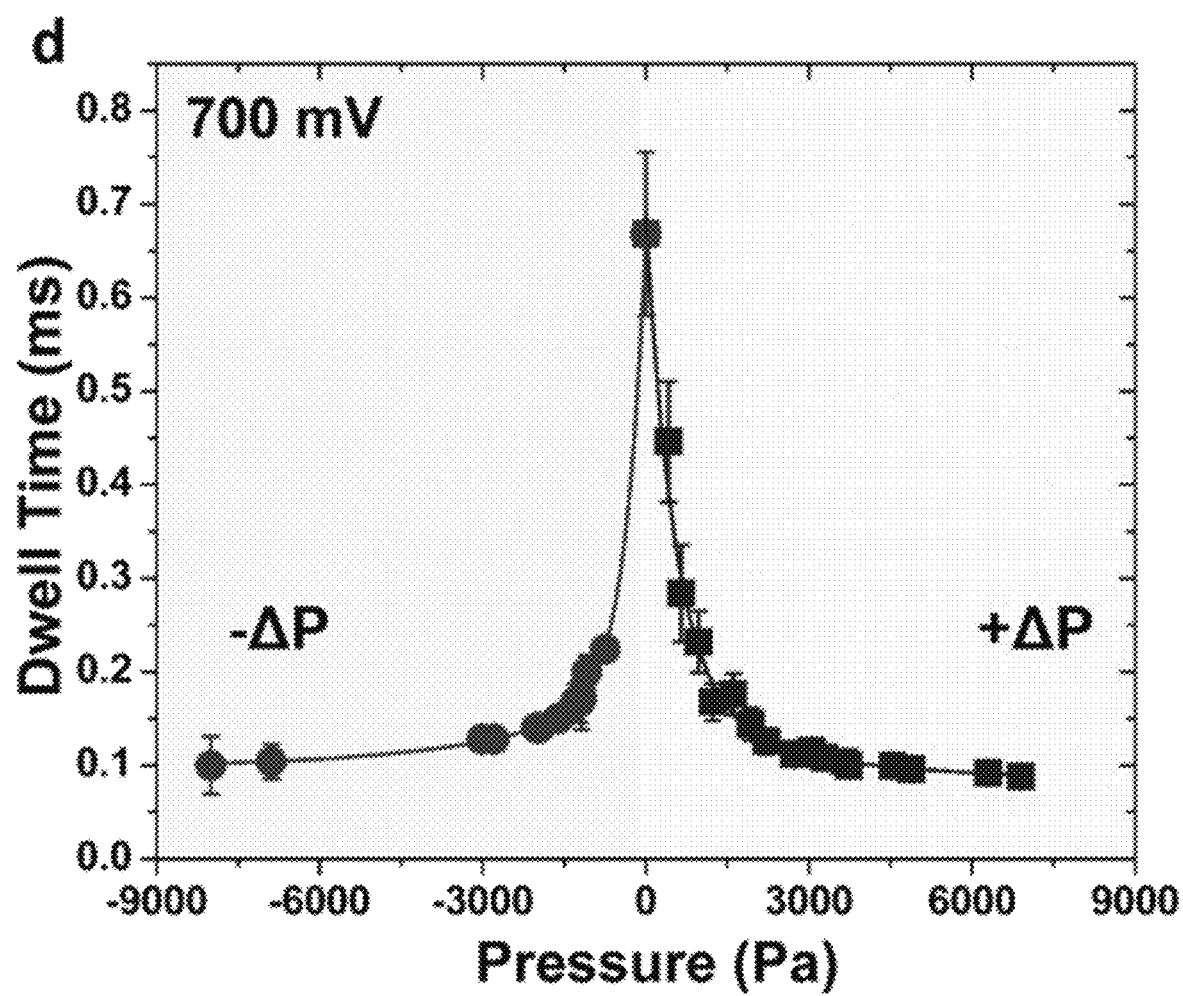
Figure 4E:
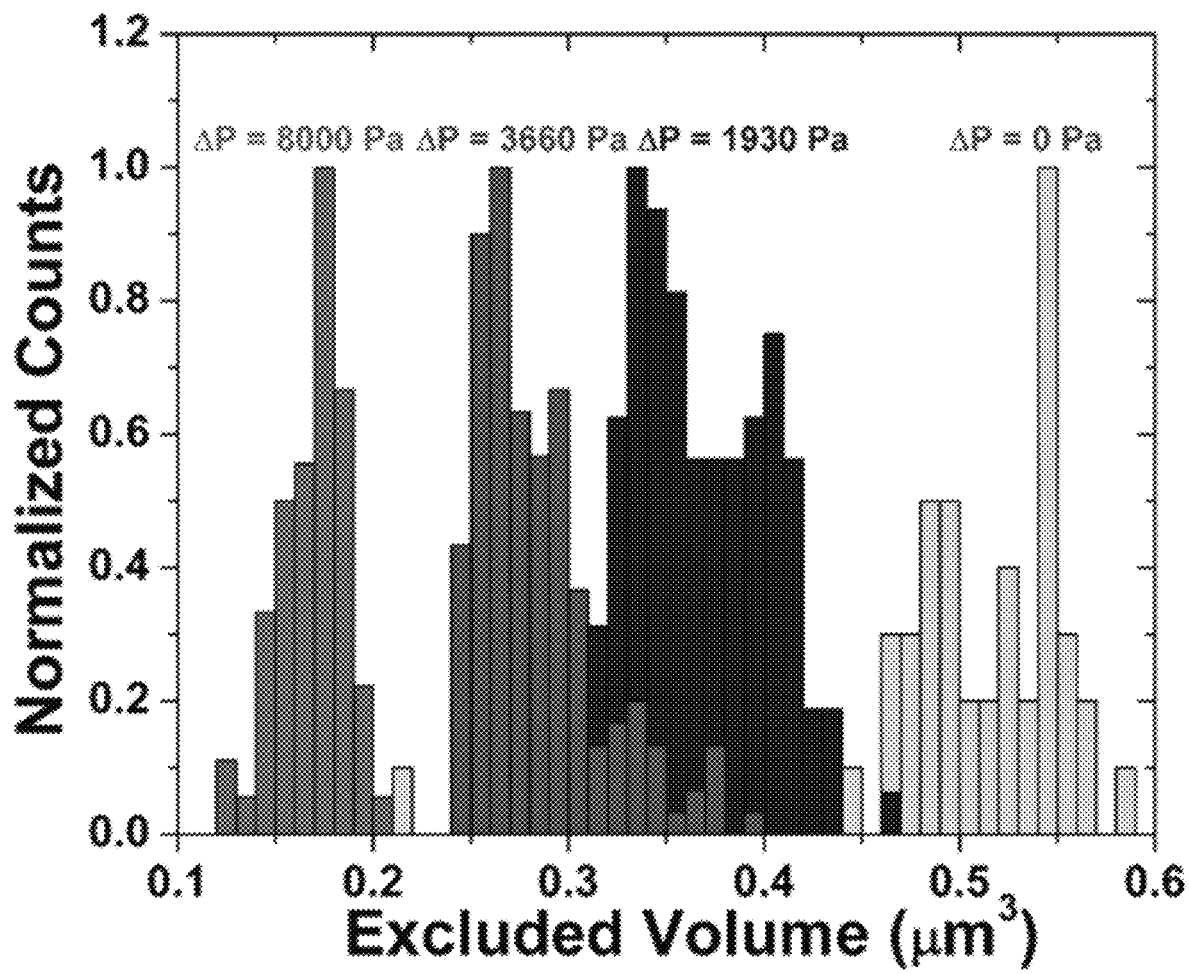
Figure 4F:
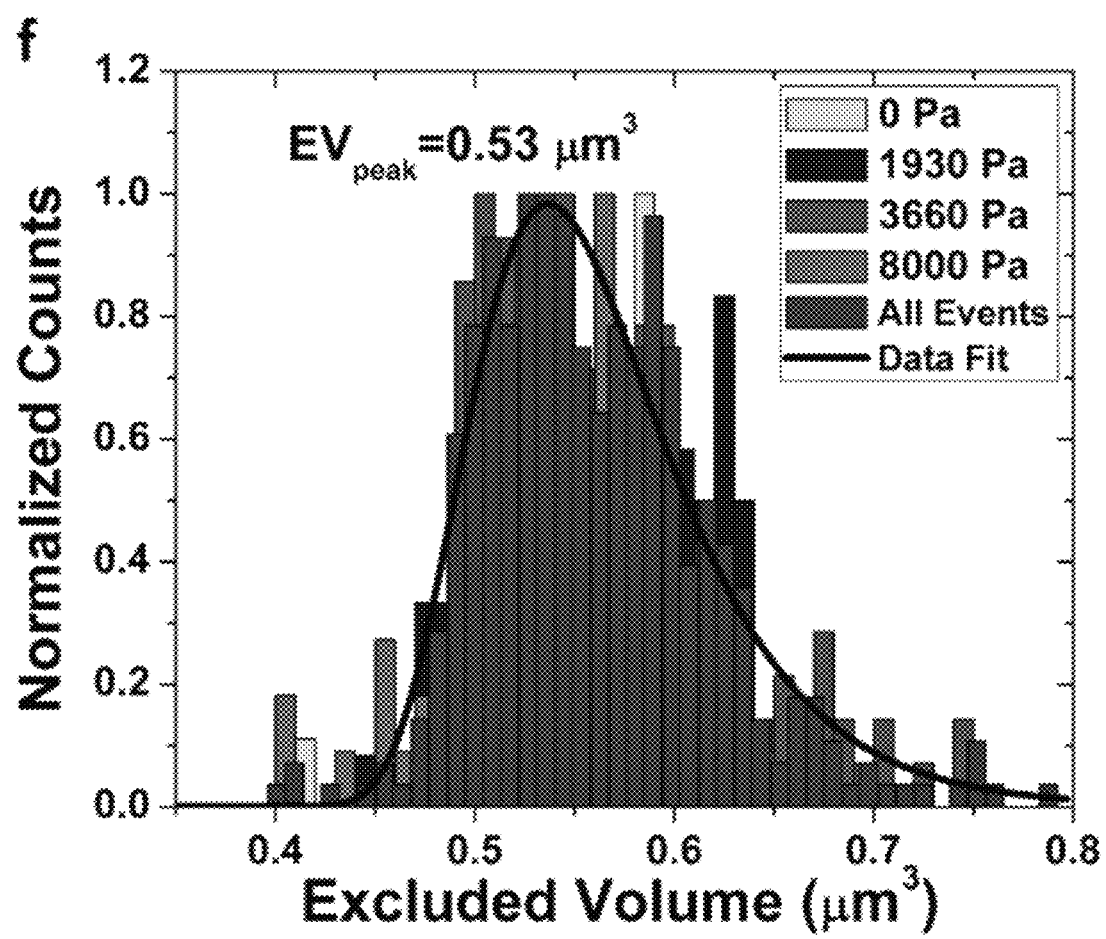

Excluded volume is another metric which can be calculated for each particle sing the current drop for each particle. The excluded volume is typically calculated using the equation $\Lambda = \Delta I H_{eff}^2 / \sigma V$, where $\Delta I$ is the amplitude of current drop, $H_{eff}$ is the effective length of the pore, V is the applied voltage and $\sigma$ is the conductivity of the electrolyte. However, the modulation of the current drop with pressure will inevitably lead to a changing excluded volume; not possible with a solid-state particle. To demonstrate the degree of error introduced in this calculation, the excluded volume was calculated without any corrections. The least known parameter in the conventional excluded volume equation is $H_{eff}$, which is difficult to find due to the tapered geometry of the pore. Since the volume of the translocating polystyrene microspheres are known, the translocation data itself (i.e. $\Delta I$) can be used to estimate the $H_{eff}$ for the pore in use. The $\Delta I$ for translocation at 0 Pa was considered for determining $H_{eff}$ which was obtained to be 8.86 μm. The excluded volume was calculated for four different positive pressure values ranging from 0 Pa to 8000 Pa. The resultant data is shown in FIG. 4e. It can be seen that the discrepancy in excluded volume equation leads to four different populations at four different pressures which is an inaccurate assessment. Therefore, the equation of excluded volume needs to be corrected to consider the effects of pressure. The modified excluded volume equation for the pressure induced flow is given by $$\Lambda = \Delta I H_{eff}^2 / \sigma [V/(1+\varphi \Delta P)]$$

where $\Delta P$ is change in pressure and $\varphi$ is a fitting constant. The value of $\varphi$ is pore specific and in our case, it was set to $2.75 \times 10^{-4}$. The corrected excluded volume under different pressure is shown in FIG. 4f which represents the true excluded volume under pressure induced flow.

2. Pressure-Controlled Recapture of Microspheres and Single Cells

Figure 5C:
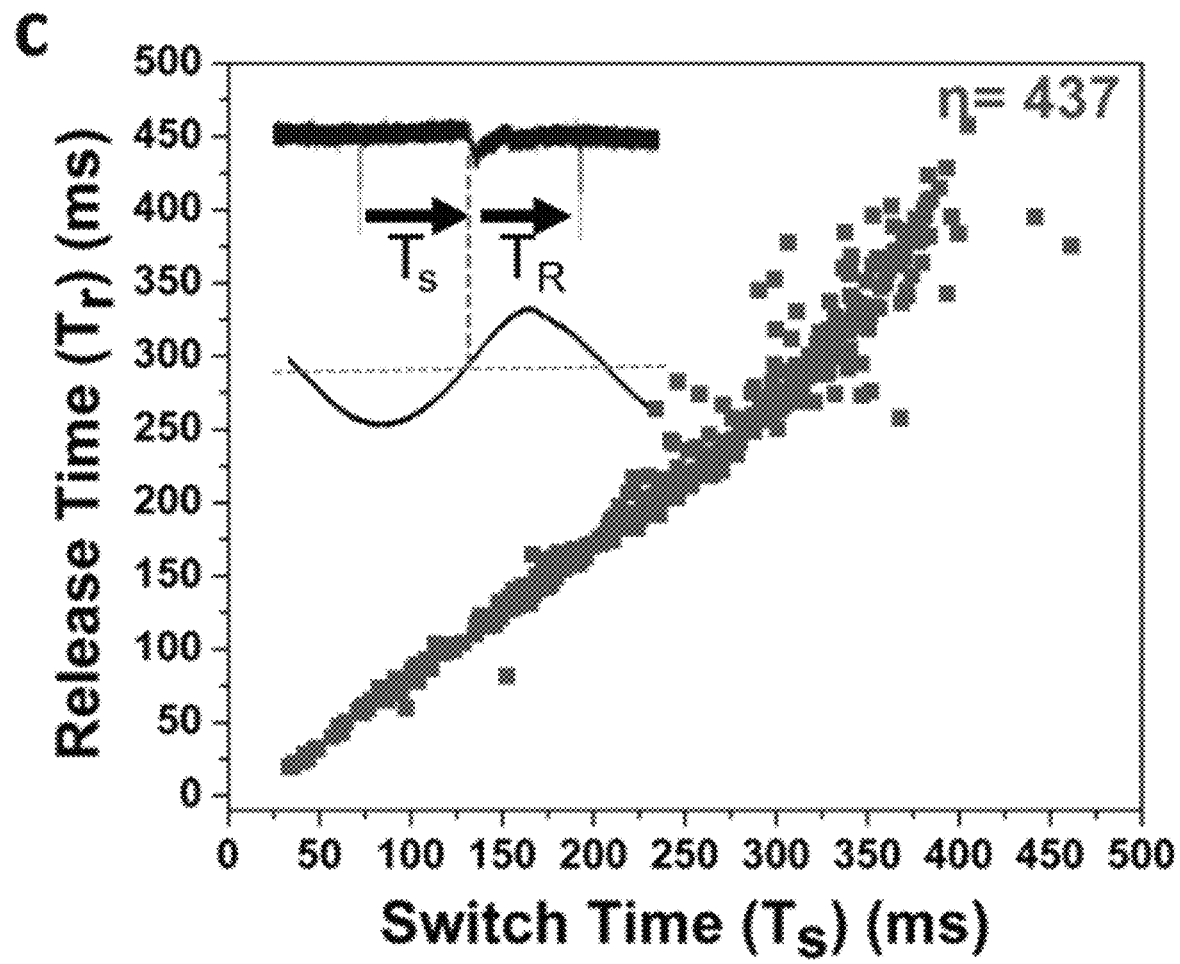

The flow reversal under the influence of pressure can be used for recapturing single particles inside the nanopore. The recapturing of polystyrene microspheres in the nanopore was performed by tuning the pressure and keeping the voltage constant at 800 mV. The applied pressure was a sine wave with amplitude ±3000 Pa and 1 cycle per second. The multiple recapture of microspheres was obtained and a characteristic signal is shown in FIG. 5(a). During the sine pressure wave, the microspheres are captured by the micropipette during the negative pressure cycle and then released out of the micropipette to the cis chamber during the positive pressure cycle. The resistive pulse is obtained every time the microsphere passes through the pore. One microsphere is sensed two times in the pore during one sine pressure wave cycle. The detailed view of the event characteristics for inward and outward translocation events of microspheres is shown in FIG. 5(a, insets). The shape of the events are a function of the pore geometry and thus the in and out events can be distinguished solely on the event signature. Multiple recapture of the same microsphere can be obtained by fine-tuning the time of sine wave, negative and positive pressure values and the concentration in the cis chamber. For each capture-release event pair, the switch time ($T_s$; defined as the time between the capture of a microsphere during a negative pressure cycle and pressure reversal) and release time ($T_r$; defined as the time between pressure reversal to microsphere release in the cis chamber during positive pressure cycle) was analyzed. A linear correlation was obtained between $T_s$ and $T_r$ as shown in FIG. 5(c). The occurrence time of an inward event during the negative pressure cycle is not fixed and events appeared randomly, while the outward event depends upon the inward event time. Since the event appeared randomly at all times during negative pressure cycle, a linear trend in $T_s$ vs $T_r$ is obtained. Unlike the conventional voltage-based recapture studies, the flow reversal was obtained by pressure reversal and all capture and release events were recorded at a single voltage (i.e. 800 mV). The pressure-controlled recapture overcomes the limitation of voltage reversal recapture since the baseline variation is minimum and there is no time gap where events cannot be detected due to capacitance.

Figure 5D:
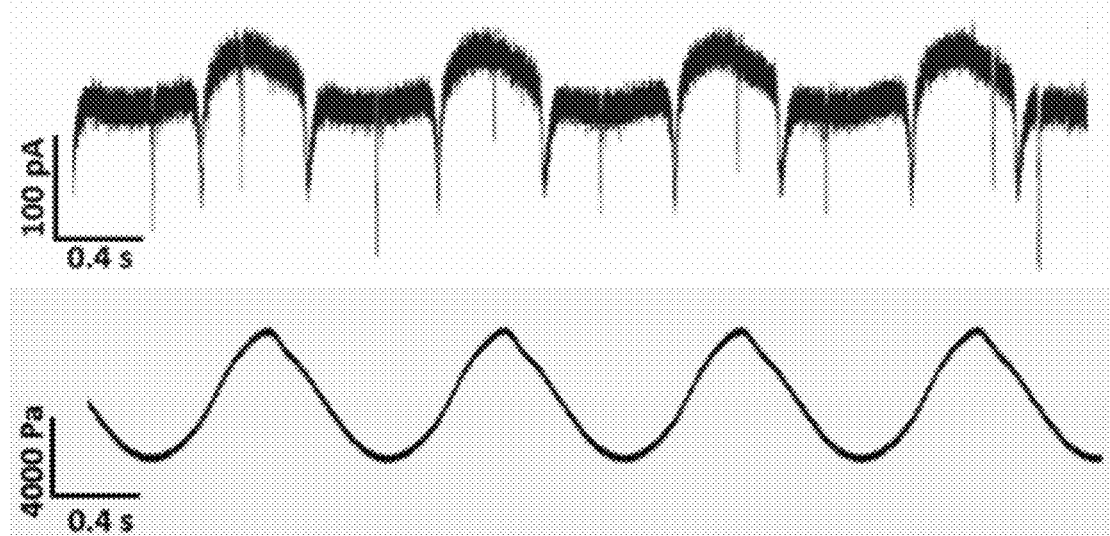
Figure 5E:
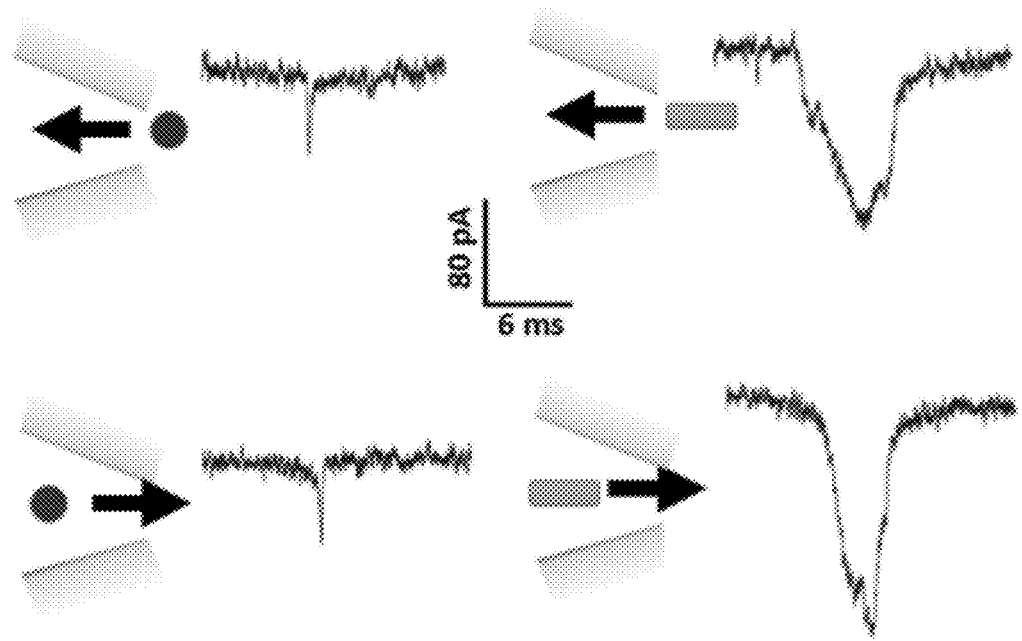

We further examined the pressure-based recapture in a mixed biological population, a mixture of two bacterial species of different morphologies were translocated and recaptured through the pore under applied pressure. The spherical *Micrococcus luteus* and rod shaped *Serratia marcescens* bacterial species were cultured together and the mixed population was used as analyte. Pressure was applied as a sine wave with amplitude ±3000 Pa, 1 cycle per second, and a voltage bias of 600 mV was applied for ionic current measurements (FIG. 5d). We observed two distinct current drop signatures; one for each species of bacteria. The current signature for the spherical bacteria had a smaller amplitude and dwell time inside the pore compared to the rod-shaped bacteria (FIG. 5e). As shown in FIG. 2(b), both the bacterial species have similar cross-sectional diameters of ~1 μm, however the length of the cell also contributes to the overall reduction of the current. COMSOL simulations were performed to independently verify that cross sectional area of the cell body as well as the length of the cell contribute to the blocking of current. Indeed, this analysis could reproduce that the rod-shaped bacteria produces higher current drop as compared to spherical bacteria of same cross-section.

Figure 5F:
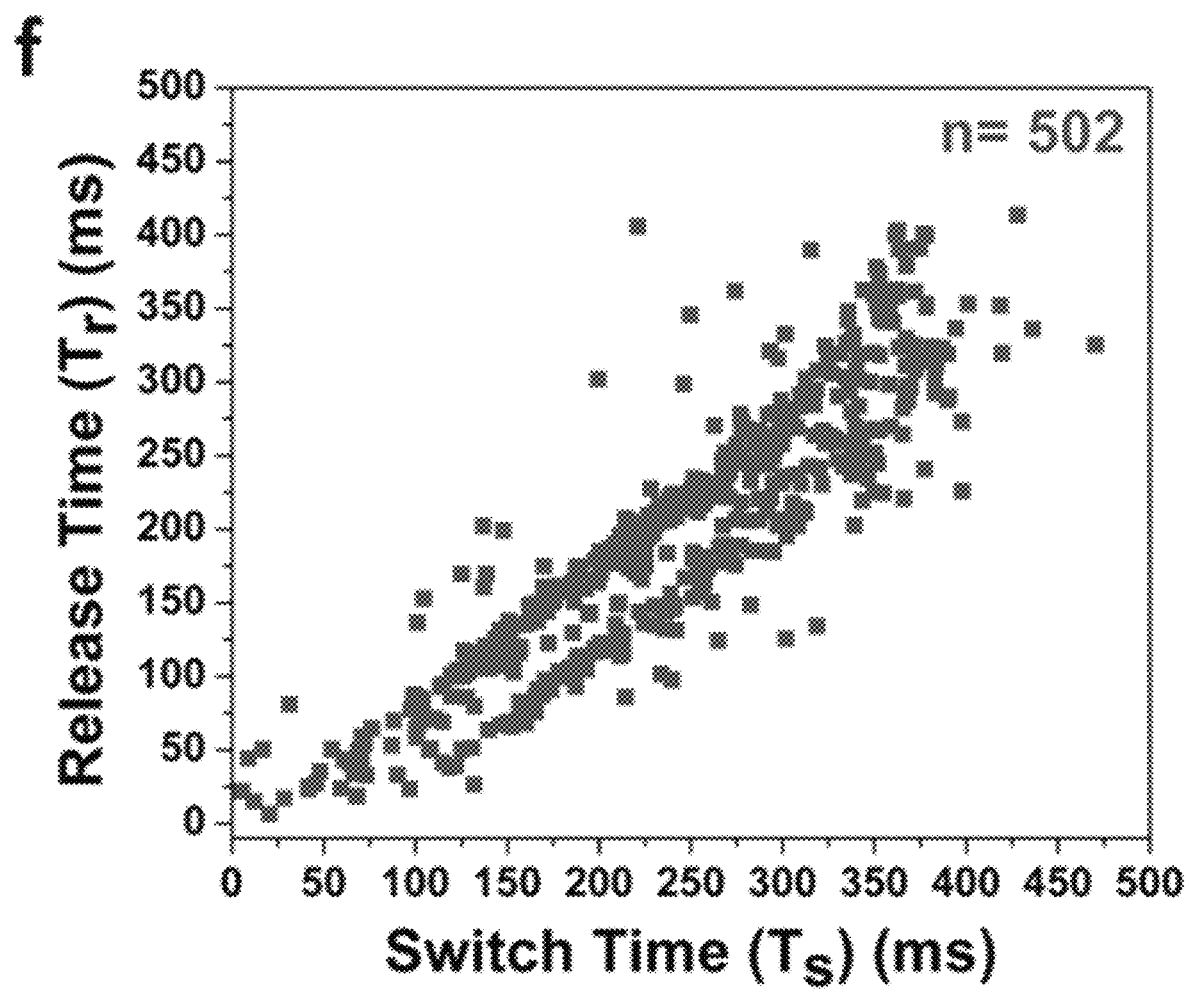

Similar to the microsphere translocation data, the switch time and release time of bacterial recapture show a linear positive correlation during the application of a sine pressure wave. Interestingly, for the mixed microbial population, the $T_s$ and $T_r$ plot shows two populations arranged parallel to each other (FIG. 5f). Based on this plot, we postulate that (1) the two populations represent the two species of bacteria and (2) that cell mass differences between the species lead to cell-specific recapture kinetics. The density and volume of a cell are the biological parameters which influence whole cell mass and are useful indicators of cell identity and potentially cell state. In terms of cell identity, FIG. 2b shows the size of each cell type. Assuming spherical and cylindrical shapes, the cell volumes correspond to 0.52 and 2.75 μm³, respectively. Density is a more complex biological parameter which varies with cell composition (i.e. lipid, protein, carbohydrate, and DNA content) over time. Lipids have the lowest density (nearly the same as water), followed by protein (Jain et al., *Nat. Biotechnol.* 36, 338-345 (2018), starch granules (Noakes et al., *Nat. Biotechnol.* 37, 651-656 (2019), and then RNA and DNA(Si & Aksimentiev, *ACS Nano*, 11, 7091-7100 (2017); Sharma et al., *Nat. Commun.* 10, 1-9 (2019) which is nearly twice the density of water. Despite the genome size of *Serratia marcescens* being roughly double that of *Micrococcus luteus*, the transcriptional activity of each cell and thus the RNA content is too difficult to predict. For estimating species-specific cell mass, we assumed a common cell density (Gershow & Golovchenko, *Nat. Nanotechnol.* 2, 775-779 (2007)[5] of 1100 kg/m³. If only mass differences due to cell volume are considered, we calculate the mass of *Micrococcus luteus* and *Serratia marcescens* as 0.576 and 3.02 picogram, respectively. In order to establish that recapture kinetics are mass-specific, discriminating cell types using the electrical signals was undertaken.

3. Identifying Mixed Population of Cells

Figures 6A, 6B, 6C:
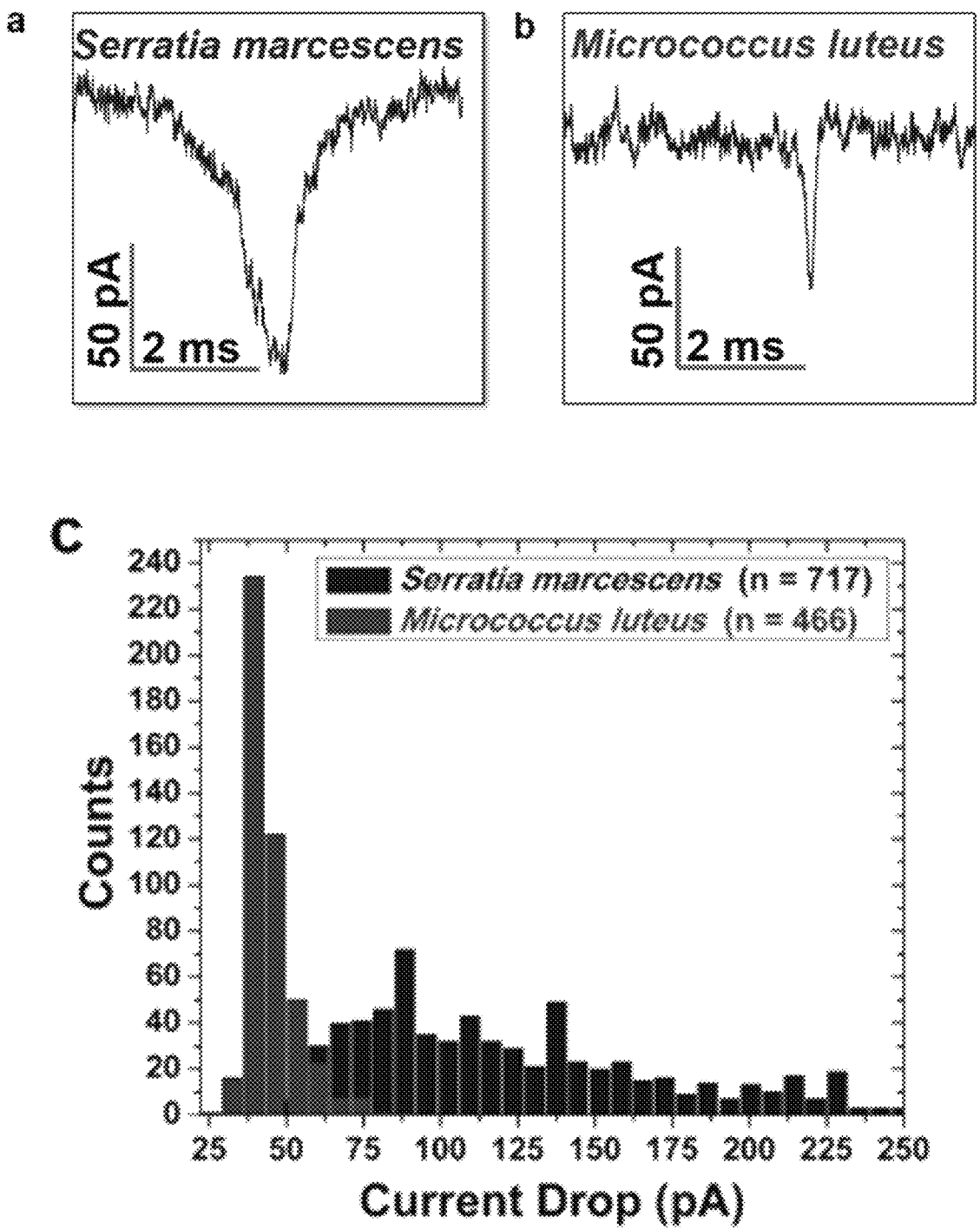
FIGS. 6A-6H. Identification of individual bacterial species in a mixed population.
Figure 6D:
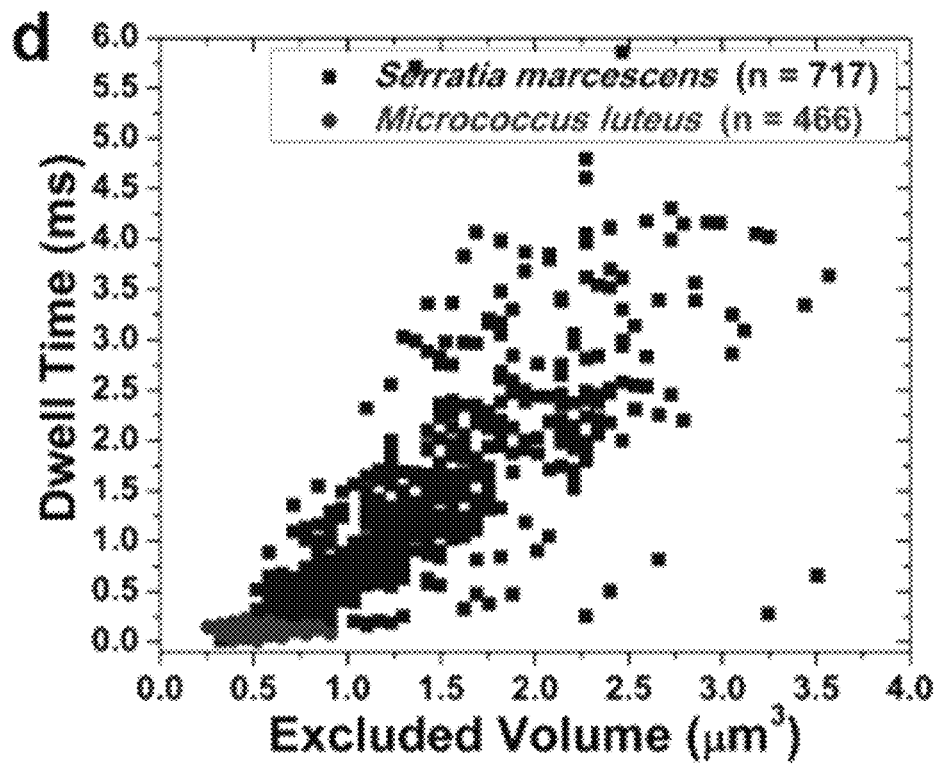

The two distinct event signatures during the bacterial recapture studies and the simulation results hinted towards the possibility of individually identifying each bacterial species. However, the event characteristics data under a sine pressure wave cannot be used directly for population statistics due to the occurrence of events at different pressure and the effect of pressure on current drop and dwell time as shown earlier. In order to individually identify two bacterial species, the bacterial species were translocated from trans chamber to cis chamber at fixed pressure (50000 Pa) and fixed voltage (600 mV). A relatively high pressure was used to avoid frequent clogging of pore at lower pressures. It is important to note that pore clogging was not significant during sine pressure wave studies because the frequent pressure reversal unclogs any potential blockages of the pore. The two distinctive current signatures were again obtained for fixed pressure translocations. A template-matching algorithm was specifically made to do this analysis and was applied on the entire event population. Two templates corresponding to two distinctive current signatures were used for identifying and associating events with each bacterial species. The templates used for analysis are shown in FIG. 6(a-b). On the basis of simulation results, the template with higher current drop was associated with the rod-shaped bacteria *Serratia marcescens* and the template with small current drop was associated with spherical *Micrococcus luteus*. A custom MATLAB script was used to identify events similar to specified template. The dwell time and current drop data was extracted for events identified under each template. The current drop clearly shows two distinctive populations as shown in FIG. 6(c). The current drop histogram for *Serratia marcescens* shows a more scattered distribution as compared to *Micrococcus luteus*. The median current drop for *Serratia marcescens* and *Micrococcus luteus* was 109.86 pA and 42.72 pA, respectively. The scatter plot with dwell time shows higher dwell time for *Serratia marcescens*. The relatively high scattered distribution for *Serratia marcescens* is possibly due to presence of flagella and size variation (i.e. length of the rod). The excluded volume for both the bacterial species was calculated using the above mentioned modified excluded volume equation to consider the effect of pressure. The previously obtained values of $H_{eff}$ and $\varphi$ which were calibrated using microspheres were used for excluded volume calculations. The dwell time vs excluded volume also shows two distinctive bacterial populations (FIG. 6d).

Figure 6E:
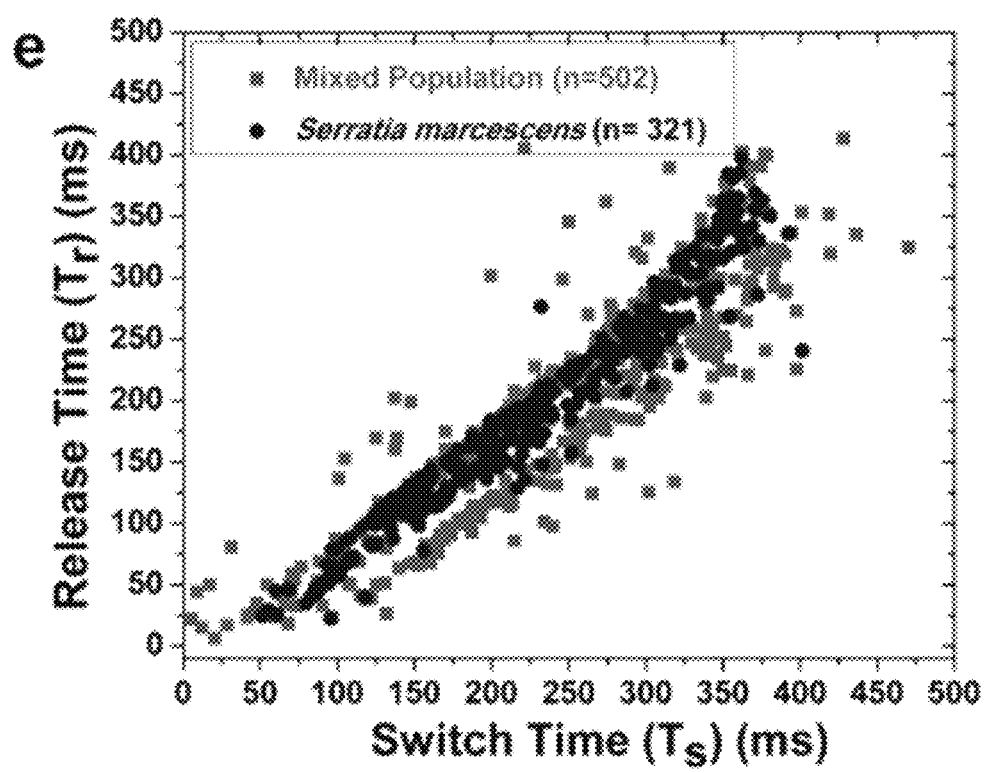

Further, to identify the two linear populations in bacteria recapture $T_r$ vs $T_s$ plot, a template-based analyses was carried on the sine pressure wave data set using the template specific for *Serratia marcescens* and respective $T_r$ and $T_s$ were extracted. The resultant $T_r$ vs $T_s$ shows one linear population which was overlapped with all events. As shown in FIG. 6(e), the data points specific to *Serratia marcescens* perfectly overlaps on one of the linear distributions in the data set of mixed population. This data successfully identifies the bacterial species responsible for each of the linear population in pressure-controlled recapture and shows that *Serratia marcescens* was recaptured slower (shown by a longer release time $T_r$) than *Micrococcus luteus* for the same switch delay ($T_s$).

To understand the role of mass within our system, an analysis of forces exerted on the cell body was performed. Fluid flow produces drag or viscous forces on the cell which is the dominant force as demonstrated by the ability to recapture a cell by flow reversal. Although fluid flow is dominated by the applied pressure, there is a small contribution from EOF (discussed previously). The voltage applied to the pore also produces an electrophoretic force on the negative cell body, albeit small compared to drag forces. A constant positive voltage is applied inside the pipette, therefore the electrophoretic force is in the same direction as the drag force during the initial translocation, and opposing the drag force during recapture. Based on the average electrophoretic mobility of *E. coli* (~1.2 µm cm $V^{-1}s^{-1}$; *E. coli* is similar in size and shape as *Serratia marcescens*) as well as the electric field inside the pore, the velocity contribution stemming from the applied voltage is only 0.6 mm/s as compared to the pressure-induced flow velocity of 19.3 mm/s at a relatively low applied pressure of 1000 Pa.

Based on the shape of *Serratia marcescens*, the translational drag coefficients for rod-shaped versus a spherical species would be higher for the rod-shaped species (Plesa, et al., *Nanotechnology* 24, 475101 (2013). The fold-difference however is typically on the order of 1.5 to 2-fold, which is relatively smaller than the mass change due to the increased volume of a rod-shaped cell (rod-shaped cells would have greater than a 5-fold increase in mass). Indeed, the drag force for a rod and sphere located at the same position inside the capillary was 8.56 pN and 15.1 pN, respectively. Despite the higher drag force on *Serratia marcescens*, the larger mass leads to a lag between fluid velocity and cell velocity and an upward shift in these cells in FIG. 6e.

Figure 6F:
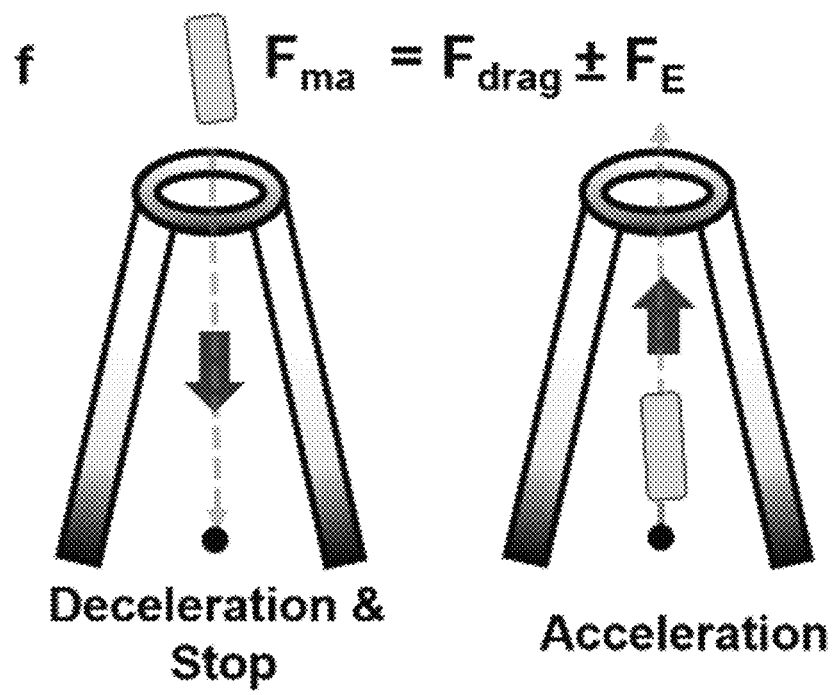
Figure 6G:
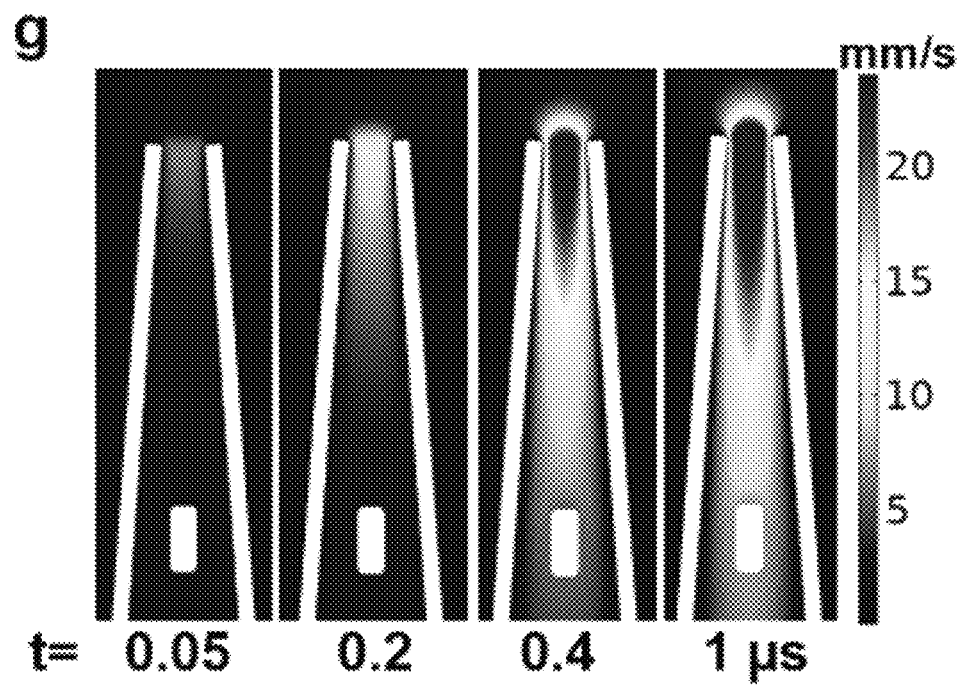
Figure 6H:
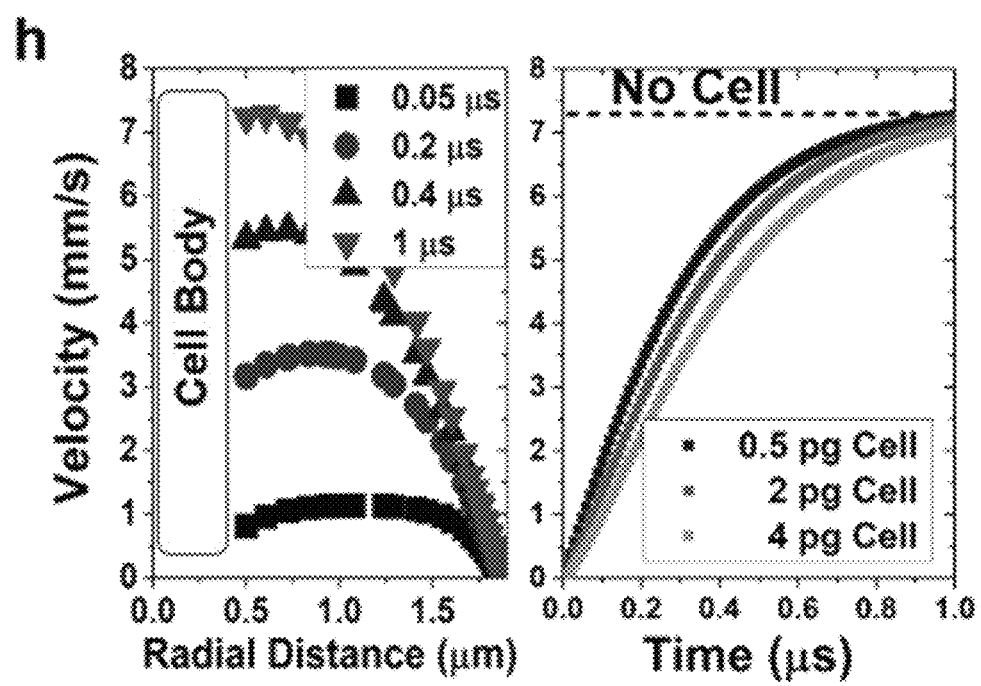

The difference in $T_r$ values at equal $T_s$ values is due to the difference in size, mass and volume of the cells in the two populations. As stated earlier the magnitude of applicable forces governs the acceleration and deacceleration of cells leading to identification of different population (FIG. 6f-h). Specifically, a time-dependent analysis using finite element methods (FEM) was performed to further elucidate the impact of the flow field near the pore. By integrating the force balance equations (FIG. 6f) into the model, the point at which a cell is captured and the flow is reversed is modelled (i.e. fluid and cell are assumed stationary). As the fluid in the capillary begins to increase velocity, drag forces are applied to the cell leading to acceleration. The rate of acceleration is modulated by the individual cell's mass. It is rather important to note that only a small fraction of the time (roughly 1 µs) was modelled and the cell actually is continually lagging the fluid during a pressure-induced flow (FIG. 6h). The continual lagging of a cell based on its mass is due to the high velocity gradients produced by a micro-scale constricted aperture. Mass-dependent velocity lagging occurs whenever a cell must accelerate and decelerate which is a condition which is always met in our set-up (both during constant pressure experiments and sinusoidal pressure waves).

4. Efficiency of Pressure-Based Recapturing

Pressure offers several unique advantages over electrophoretic recapturing such as no time gaps in the ability to sense a translocation (i.e. no capacitance spike) and the ability to capture and recapture un-charged entities. Another limitation is the short window of time wherein recapture is possible (i.e. before diffusive forces become dominant). By demonstrating that flow-based mechanisms are dominant over electrophoretic, we predicted that the drag forces dictating the capture process of a particle extend further into the solution chamber, leading to greater recapture efficiency. To study the efficiency of recapture, a new method of applying the pressure reversal was devised which eliminated the unpredictable nature of the initial capture event. During the application of a sine pressure wave, the analyte can be captured at any time during the negative pressure cycle and recaptured during the positive pressure cycle (i.e. a capture event early in the negative pressure wave results in a recapture at the end of the positive pressure wave). The release or recapture time ($T_r$) depends upon the switch delay time ($T_s$) but the timing of the events are random (i.e. no direct control over the release time).

Figure 7A:
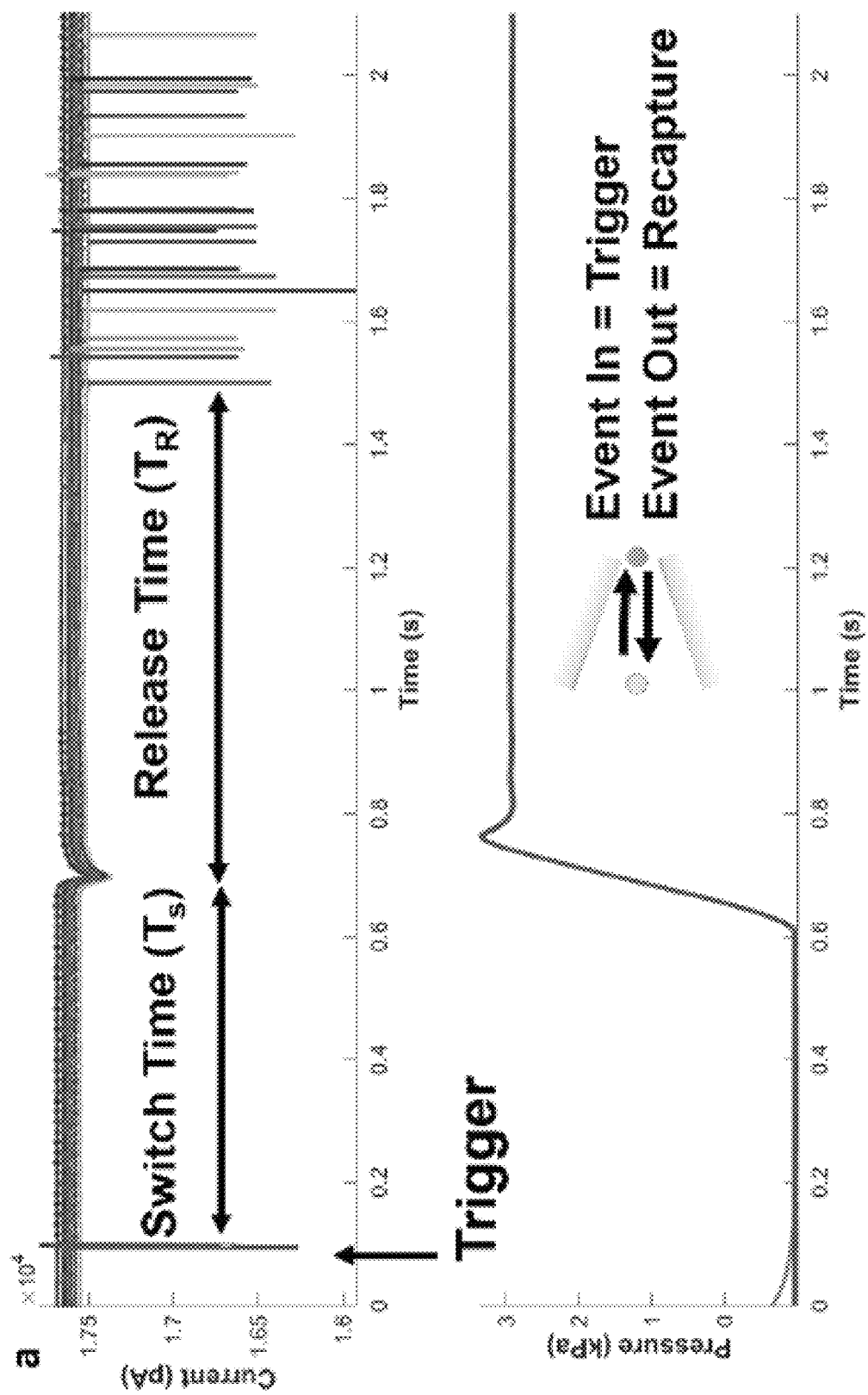
FIGS. 7A-7J. The capture triggered release of beads and cell-derived nanoliposomes.
Figure 7B:
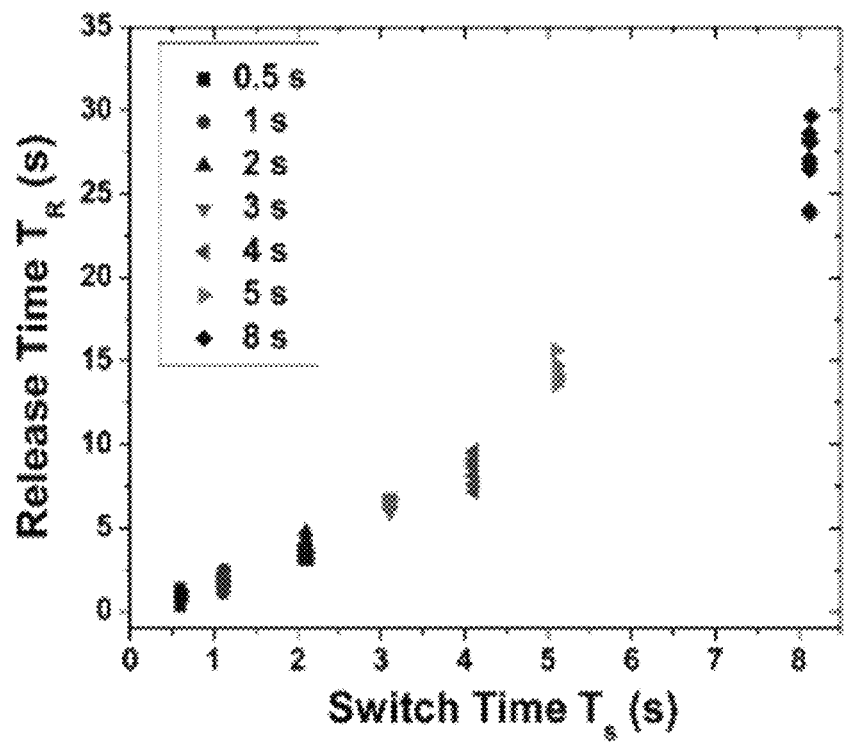
Figure 7C:
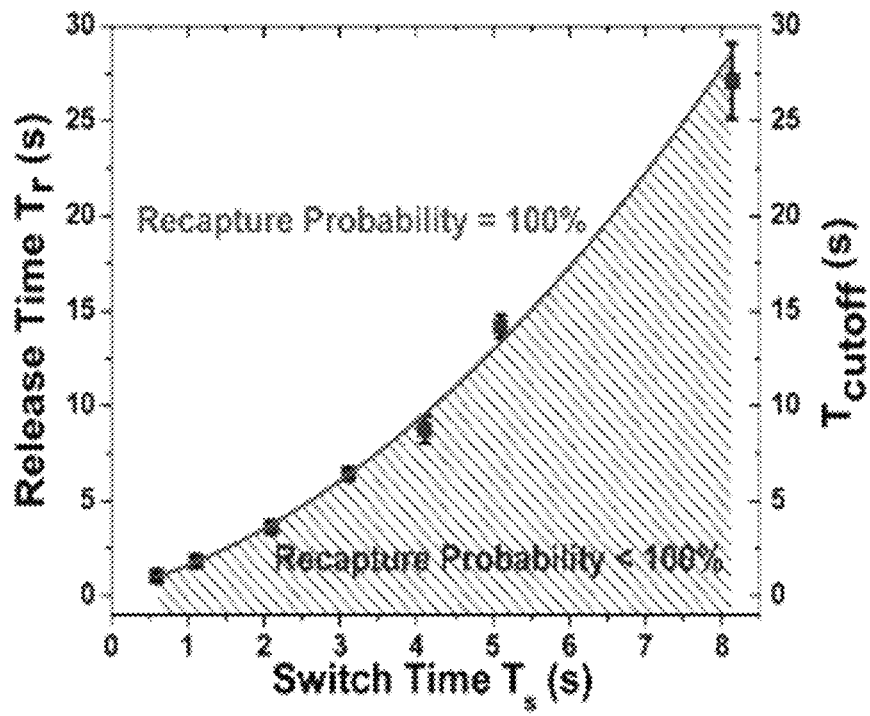

In order to have direct control over the pressure switch delay time, an event-triggered pressure reversal software was developed using real-time event detection. By detecting an event, and waiting a pre-set amount of time, direct control over the displacement of the particle away from the pore orifice was achieved. Similar to electrophoretic recapture, a longer delay leads to larger displacements from the pore orifice and thereby a lower probability of recapture. A custom-made program was used to sense the analyte capture using the current drop and reverse the pressure, which leads to a precise switch delay ($T_s$) and release time ($T_r$) distribution. The key parameters which were utilized in these experiments were the capture pressure, release pressure, switch delay ($T_s$) and the total time for which the release pressure will be applied ($T_{cutoff}$). Polystyrene microspheres (mean diameter: 1 µm) were used to demonstrate the capture triggered release. The typical current and pressure traces for a fixed applied $T_s$ of 500 ms is shown in FIG. 7(a). A range of switch delay times (up to 8 seconds) was applied and the corresponding $T_r$ was tabulated (FIG. 7b). The median $T_r$ at every $T_s$ condition shows a second order polynomial distribution with a 100% recapture probability. Any $T_{cutoff}$ time higher than the median $T_r$ for a given $T_s$, we obtained a 100% recapture probability. On the other hand, if the $T_{cutoff}$ is less than $T_r$, the recapture rate drops due to switching the flow direction too soon to observe the release of the bead. Therefore, precise tuning of applied pressure values and the time at which pressure is switched, is necessary for achieving a 100% recapture probability.

5. Recapturing Cell-Derived Nanoscale Liposomes

Reduction of the pore diameter to the nanoscale increases the hydrodynamic resistance of the nanopore significantly and thereby decreases the ability to generate the flow rates needed for recapture. Nevertheless, using a 250 nm pore and larger pressures, recapturing of nanosized liposomes was successfully performed in this work. Red blood cell nanoliposomes (RNLs) were prepared by mechanical extrusion of human whole blood and differentially centrifuged to select out liposomes that were ca. 160 nm. Lipid vesicles are ubiquitously found across biology as well as widely used as a drug delivery vehicle. RNLs in particular are promising candidates for drug delivery since the red blood cells can be harvested from the patient directly thereby precluding many of the auto-immune interactions which occur during synthetic liposome drug encapsulation and administration and ensuring longer circulation time of the drug. However, due the variability of red blood cell lipid compositions, RNLs may require optimized extrusion parameters in the moments leading up to drug encapsulation. The nanopore technique offers a rapid, low concentration, and low volume method to obtain the size distribution of RNLs in a clinical environment where blood sampling should be minimized. Furthermore, it may be possible to probe the contents of the liposomes (i.e. successful or unsuccessful loading) using the recapture kinetics of the liposomes. This may be possible for any payload which has higher densities compared to water (i.e. RNA, DNA, and heavy metal contrast agents).

Figure 7D:
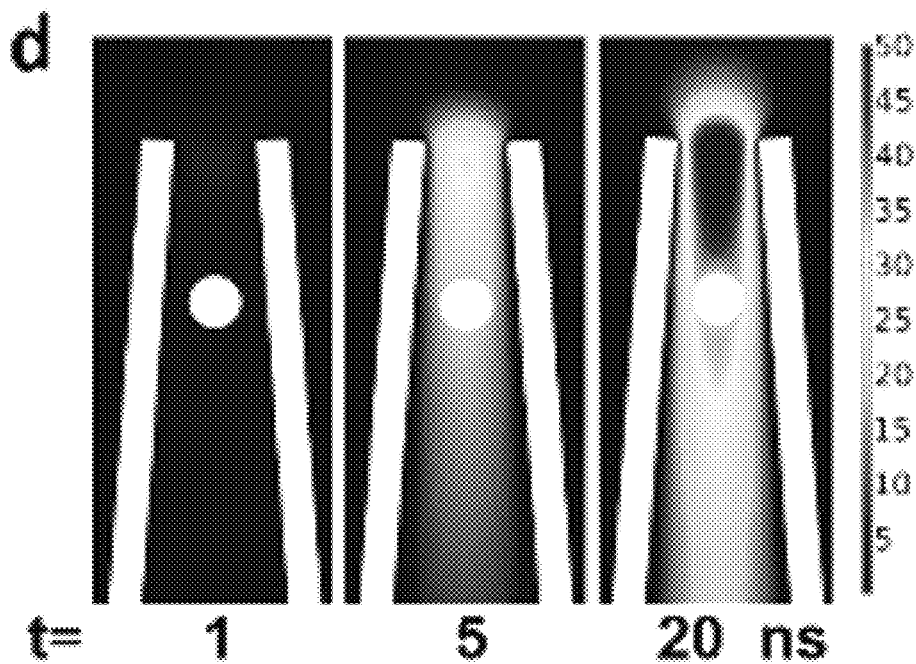
Figure 7E:
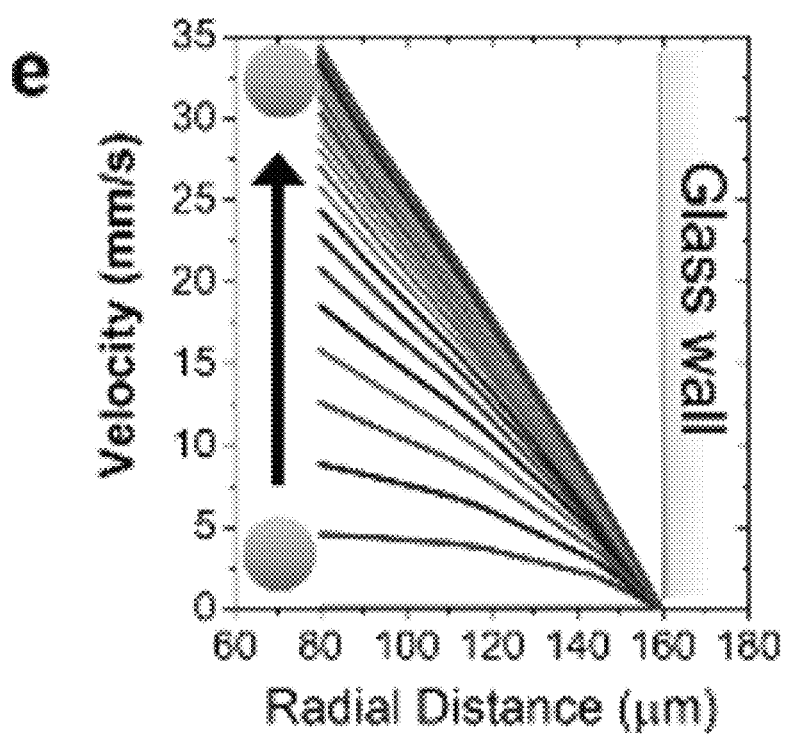
Figure 7F:
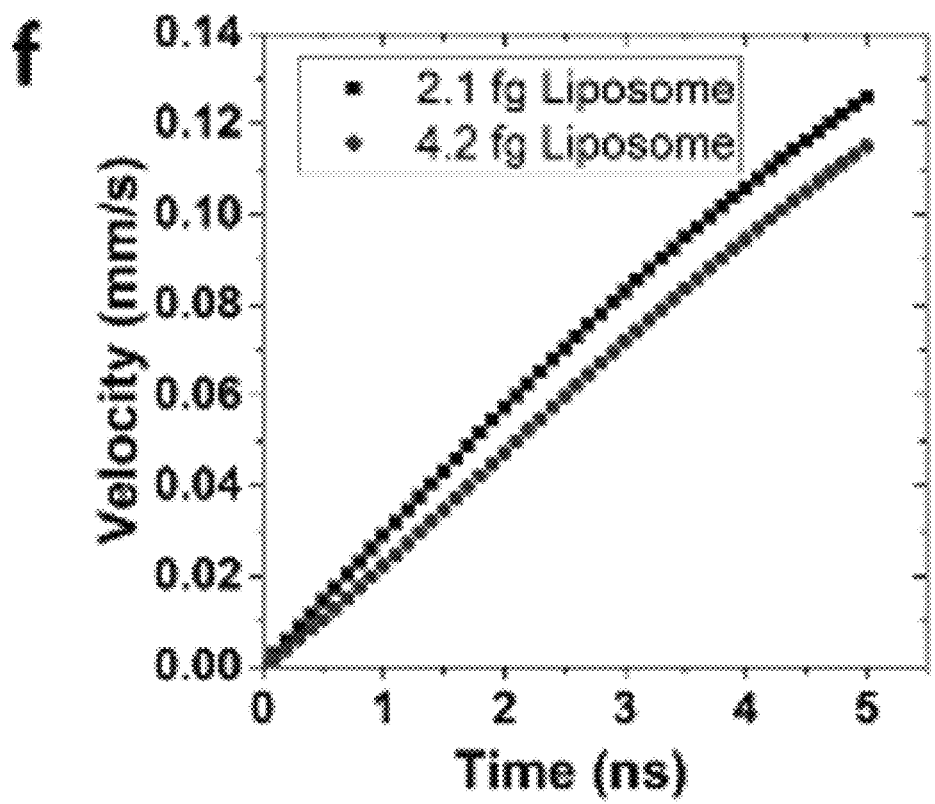

FEM models were employed with the modified nanoscale geometry and we simulated comparable mass-dependent velocity profiles when exposed to high velocity gradients near the pore. However instead of lagging the fluid velocity by microseconds, the time to accelerate the nanoliposomes was several nanoseconds (FIG. 7d-f). Although the simulations represent a single acceleration scenario where both the nanoliposome and fluid start at zero velocity, the difference in the scale of time (microseconds versus nanoseconds) is noteworthy. Since the nanoliposomes are continually accelerating and decelerating in the nanopipette, the lag time due to drag forces would be summed (i.e. integrated) throughout the transport process. One way to further increase the effects of drag, and lengthen the lag time, is to use large switch delays which would increase the integration time over which lag is occurring.

Figure 7G:
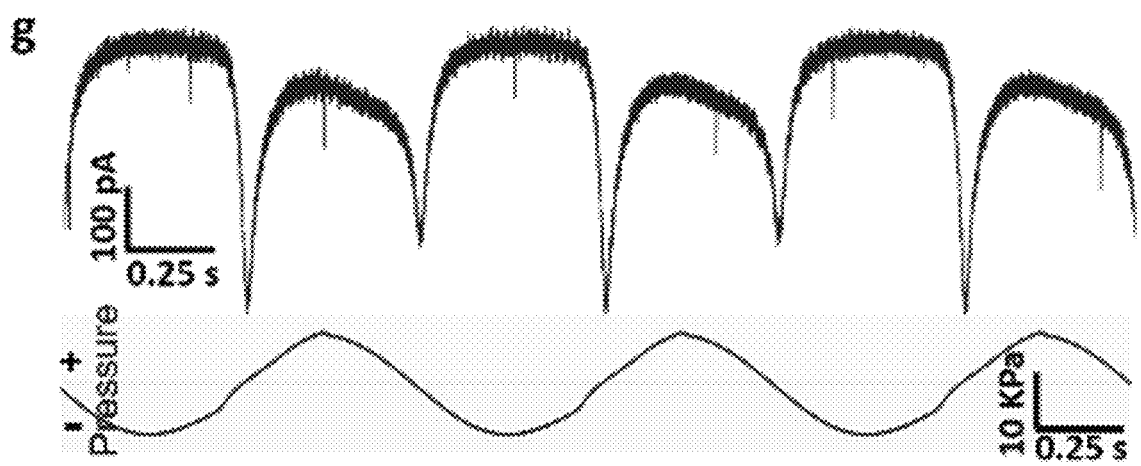
Figure 7H:
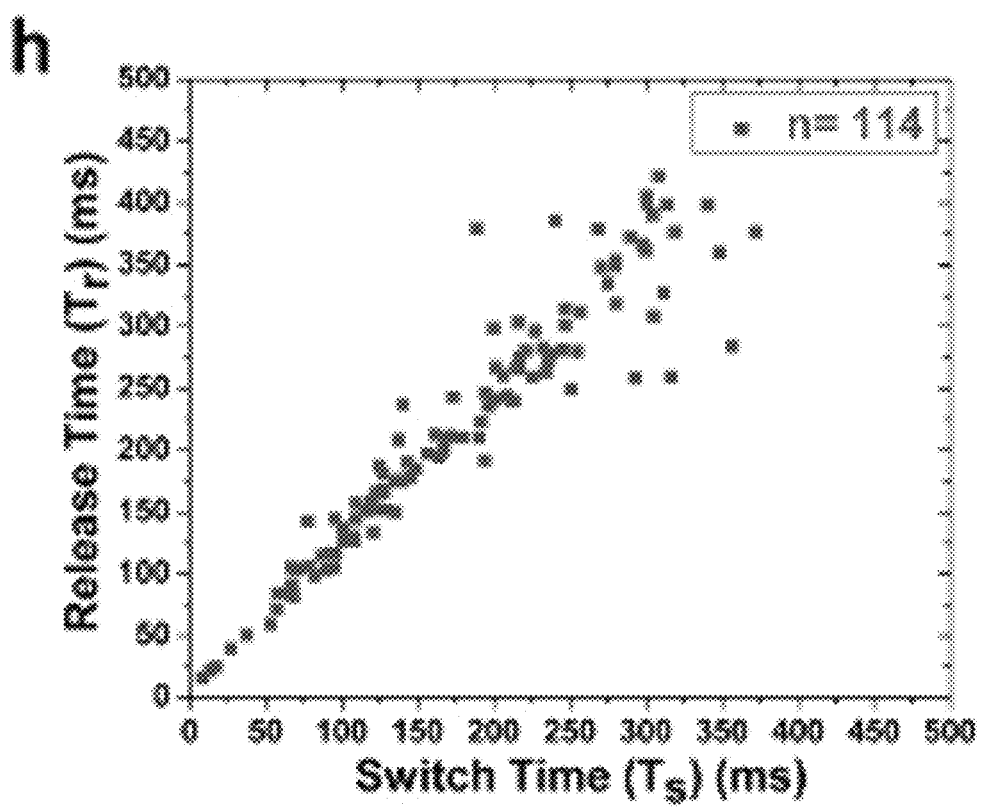
Figure 7I:
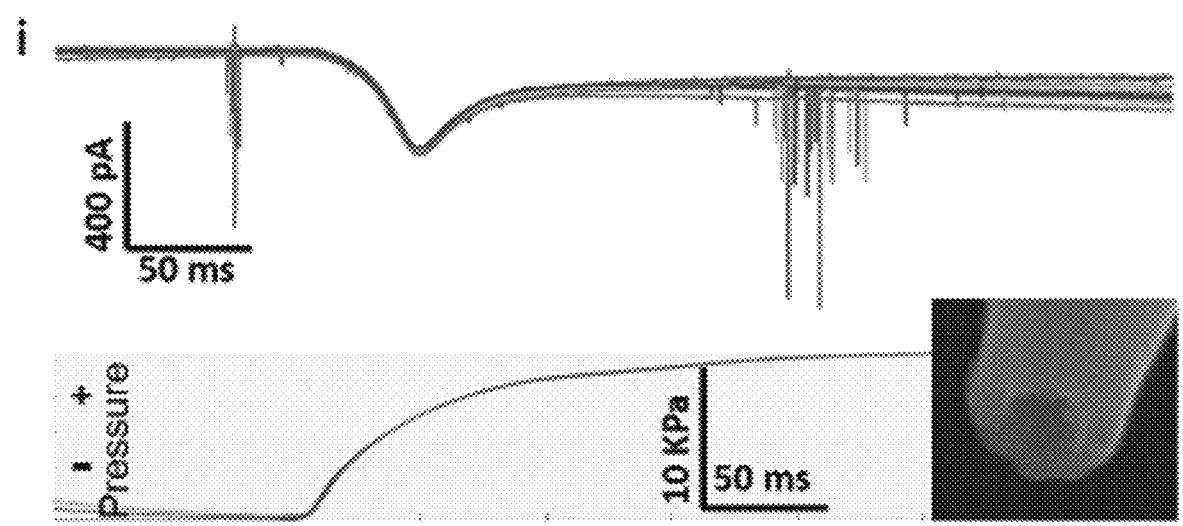

The capture and release of RNLs in a glass nanopore was studied using sine pressure wave with amplitude ±10000 Pa, 1 cycle per second, and an applied voltage bias of 900 mV. The typical current and pressure signature in FIG. 7g shows successful recapture of the RNLs. The recapture was also validated using the capture-triggered release system (representative current drop and pressure traces shown in FIG. 7i using a switch delay of ~75 ms. The $T_s$ vs $T_r$ for the sine pressure wave and the capture triggered release is shown in FIGS. 7(h and j), respectively. As expected, a linearly distributed $T_s$ vs $T_r$ was observed with sine pressure wave while a narrower distribution was obtained for capture-triggered release.

Figure 7J:
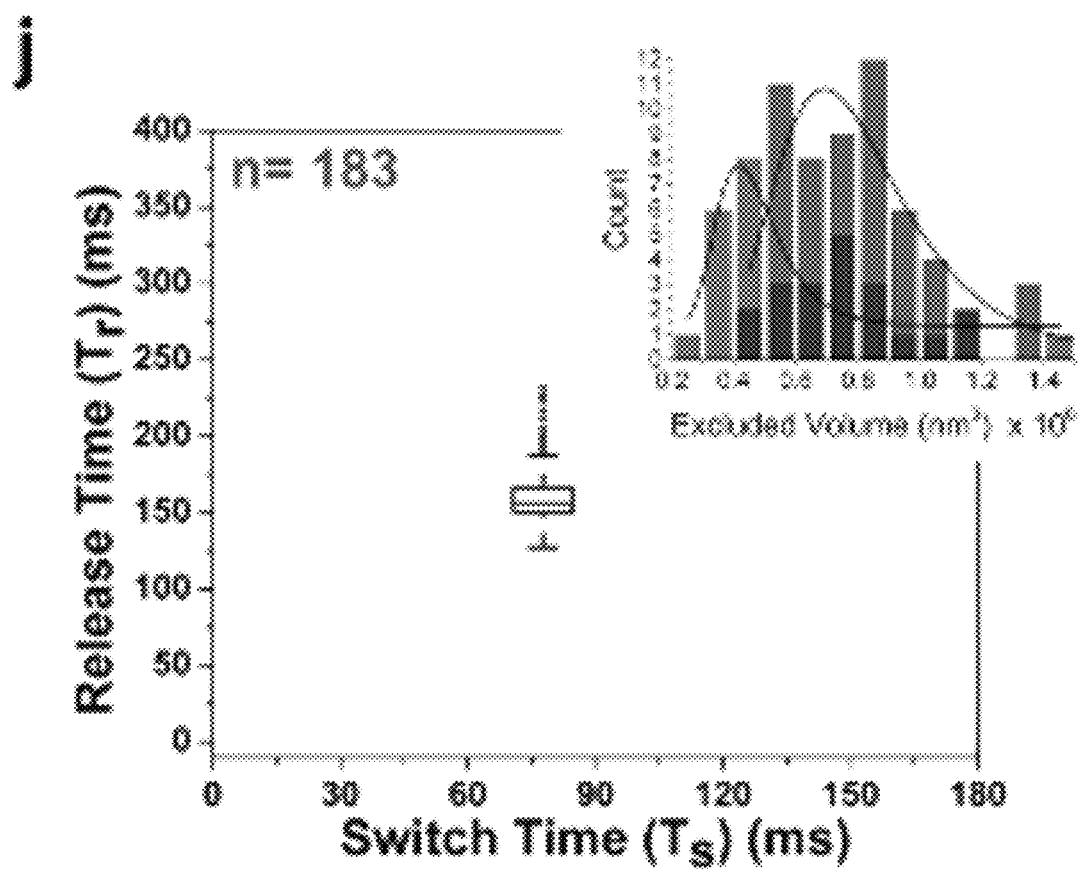

Although the mass, and therefore the mass-induced lag time in the recapturing of the nanoscale liposomes is much smaller, we attempted to test the hypothesis that larger nanoliposomes were recaptured later (i.e. longer $T_r$). While the $T_s$ values were narrowly distributed, the corresponding $T_r$ values had a Gaussian distribution. In order to test whether mass was influencing the recapture, events in the upper $75^{th}$ percentile of the $T_r$ distribution was compared to the lower $25^{th}$ percentile. Once the events were categorized, the event properties (i.e. current drop and the recorded pressure) were used to calculate the excluded volume. The inset of FIG. 7j shows the excluded volumes of these two populations. Using a significance value of 0.05 (i.e. P-value), we concluded there was a significant difference in the size and thus the mass of the two populations.

6. Nanopore Method Discriminated Empty and Drug Filled Nanoliposomes

Figure 8:
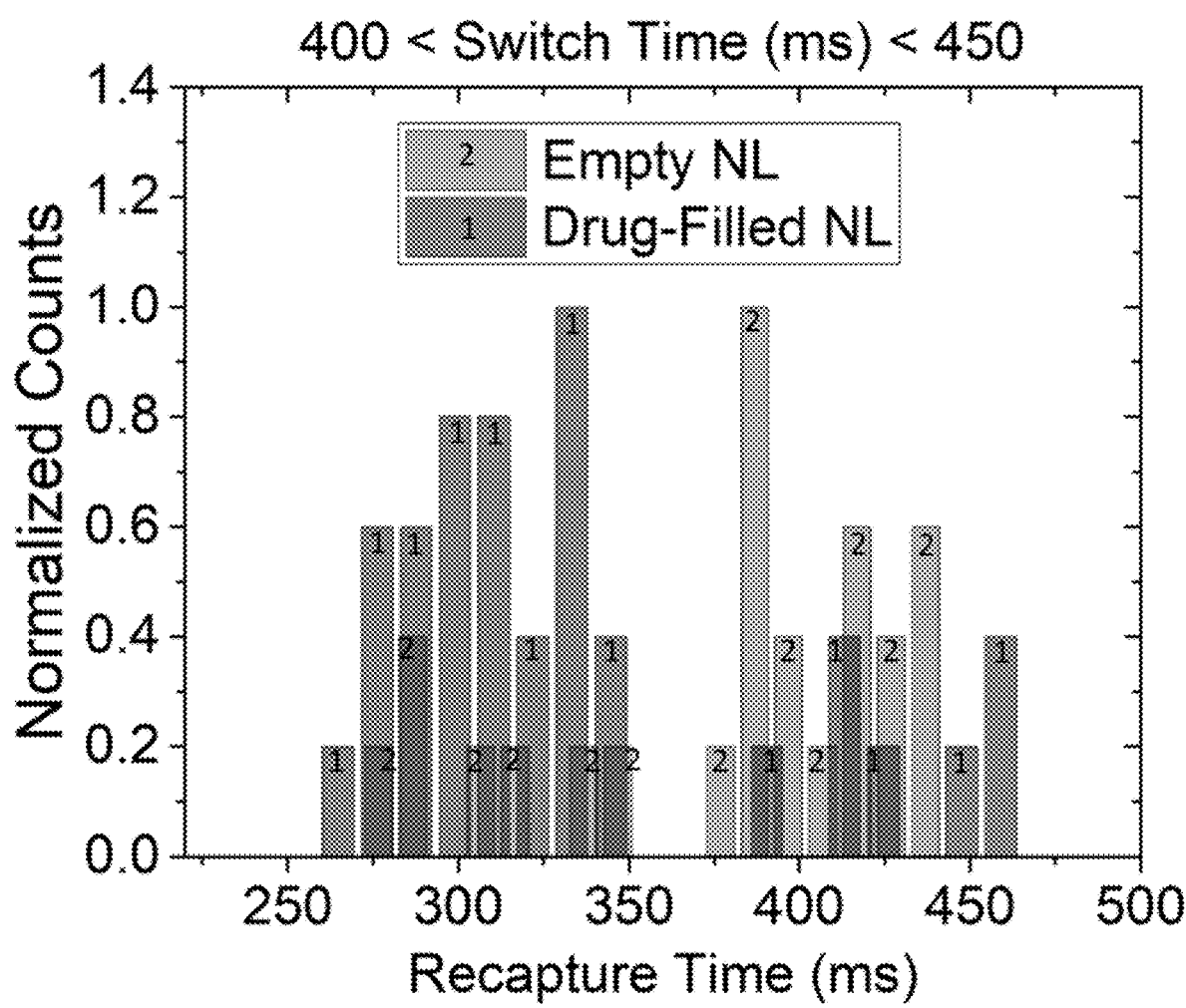
FIG. 8. Successful discrimination between the two identically sized nanoliposomes (NL): one empty (water filled), and one drug-filled with 5% salicylic acid.

Nanopipettes were fabricated to have an internal diameter of 250 nm pore and pressures of ±50 kPa were applied to the back end of the nanopipette. The 10-50 kPa range of pressure biases resulted in pressure-dominant transport of nanoliposomes (both empty and drug-filled). The capture and release of NL in a glass nanopore was studied using sine pressure wave with amplitude ±50 kPa, 1 cycle per second, and an applied voltage bias of 600 mV. Since both empty and drug-filled nanoliposomes were fabricated using the same extrusion protocol, the size of the nanoliposomes remained constant. Indeed, the current blockade depth (a metric of size) could not distinguish between the empty and drug-filled nanoliposomes. However, the recapture times did indicate a change in mass (or mass/charge ratio) that could be measured. The recapture time is expected to represent a combination of inertial effects stemming from the nanoliposomes and the influence of charge of the drug. In both cases, the drugs physiochemical properties and drug's presence inside the nanoliposomes is being measured with this nanopore tool. FIG. 8 shows the ability of this nanopore based approach to discriminate between the two identically sized nanoliposomes: one empty (water filled), and one drug-filled with 5% salicylic acid.

While micro and nanoscale particles have been passed through constricted apertures for decades and for a wide range of applications from cell counting to DNA sequencing, the utilization of alternative transport mechanisms is more recent (REFS). Here, exploration of pressure as a way to modulate or even control the direction of a translocating micro and nanoscale component was achieved. In addition to controlling the dwell time, we propose also that the capture rate (i.e. events/min) can be modulated on-demand during an experiment. Achieving higher capture rates was observed repeatedly in our experiments (i.e. with increasing pressure, the capture rate was increased with a linear dependence). Furthermore, and even more beneficial, when no events were recorded due to EOF coming out of the pore and insufficient electrophoretic force was present, applying pressure reversed the flow direction and allowed for the translocation of both microspheres and bacteria. Interestingly, due to the low Reynolds number of the constricted apertures at the micro and nano length scales, extremely efficient recapture is also possible.

The efficiency of pressure-based recapture is only limited by diffusional displacements which becomes larger at the nanoscale. Molecular recapture, for example DNA and proteins, is much more challenging and would require significantly higher pressures to generate sufficiently high fluid velocities. Also hindering the pressure-based recapture of DNA is the highly negatively charged backbone and the strong dielectric focusing of the electric field within a nanoscale aperture. Such large electric fields (ca. $10^7$ V/m) are more difficult to overcome. Recapturing neutral biological molecules and components may be possible however this needs to be investigated further. To minimize displacement due to diffusion (especially for nanoscale objects), higher viscosity buffers may also be utilized to further increase the switch time and maintain high efficiency.

Among the many physiochemical properties that apertures can measure, we have demonstrated for the first time that mass is among those properties. More work needs to be completed to ascertain the lower limits of mass discrimination as well as if true mass, rather than relative mass, can be obtained. Nevertheless, discrimination alone opens the door to many exciting prospects. Here, we demonstrated the ability to characterize cell-derived nanoscale liposomes in terms of mass and volume. The mass discrimination in particular is exciting since mass will be predominantly determined by the payload. Currently, measuring the heterogeneity in loading nanoliposomes is challenging and worth further investigation. Aside from mass and volume, our experimental setup can also precisely measure concentrations as well, which has been demonstrated by others. By applying pressure and calculating the volumetric flow rate, the event counts provided by the measurement of ionic current can yield concentrations (particles/volume of fluid). Concentration is critical for evaluating cell-derived nanoliposomes since the exact lipid properties are patient specific and even vary across time. Due to these variables, even the same procedure for making cell-derived nanoliposomes can lead to batch-to-batch variation. The prospect of using apertures as an all-in-one tool for rapidly assessing patient-derived drug delivery vehicles at the patient's bedside is certainly an exciting outcome of this work.

It is demonstrated that nanopores and micropores can be utilized as inertial mass sensors, as well as obtain information about nanoscale biological structures via ionic current recordings. The precise timing of the events (~microsecond resolution) affords the opportunity to measure mass-dependent time lags in the recapturing of micro and nanoscale biological structures. Discrimination of two bacterial species which have approximately the same cross-sectional area (0.785 $\mu m^2$) was achieved. It's further demonstrated that cell-derived nanoliposomes, and empty or drug loaded nanoliposomes can also be recaptured, albeit at higher pressures, for mass and size characterization.

Methods

Pipette preparation. The glass capillaries made of borosilicate with outer diameter 1 mm and inner diameter 0.5 mm was procured from Sutter Inc. The capillaries were plasma cleaned using a Harrick plasma cleaner PDC-001. The micropipette puller from Sutter. Model P-2000 and P-97 were used for pipette pulling. The pipettes for translocation of 1 µm polystyrene microspheres were pulled using following protocol Heat—350, Fil—4, Vel—30, Del—200, Pull—0. The translocation of bacteria was carried out on pipettes pulled using the protocol Heat—330, Fil—4, Vel—30, Del—200, Pull—0. The nanopipettes for RBC nanoliposome translocation was pulled using Sutter P-97 pipette puller. The protocol used was Heat—Ramp+5, Pull—35, Vel—75, Del—130. Pressure—500.

Sample Preparation. Phosphate buffer saline was used as target buffer throughout this study. Hyclone™ PBS 10× was procured from GE healthcare and diluted to 0.1× using DI water, ACS reagent grade, ASTM type 1 procured from Labchem. The target buffers were filtered using a 0.2 µm sterile filter discs procured from GE Healthcare. The carboxylate modified polystyrene microspheres of mean diameter 1 µm was procured from sigma-aldrich and used as a final dilution of 1:1000 in 0.1×PBS buffer.0.015% triton X-100 was added in measurement buffer and the buffer containing the microspheres was sonicated using a Branson-1800 sonicator for 2-5 minutes before the measurement.

A mixed suspension of pigmented bacteria *Micrococcus luteus* and *Serratia marcescens* was procured from Carolina Biological Supplies and cultured into a Remel thioglycollate medium. The overnight grown bacterial culture was centrifuged at 5000 rcf for 5 minutes. The resultant bacterial pellet was resuspended in 0.1×PBS. The bacterial suspension was further diluted as per requirement.

Pressure setup. In order to apply pressure to the nanopore, an electrode holder from Warner Instruments was used. The pipette was fixed into the Ag/AgCl electrode connected to the electrode holder. The pressure was applied using an Elveflow AF1 Dual Vacuum & Pressure Controller. A software-controlled pressure output was used. The pressure values were recorded in real time. For recapture experiment pressure sine wave was applied using ESI microfluidic software. A custom made Labview control system was used for pressure switching during the event triggered recapture experiment.

Measurement platform. Ag/AgCl electrodes were prepared by soaking a silver wire of diameter 0.25 mm (Alfa Aesar) into concentration bleach solution for an hour and rinsing thoroughly with water. An Axon Digidata 1550 B digitizer (Molecular Devices. CA) was used for the data acquisition. Axopatch 200B (Molecular Devices, CA) patch clamp amplifier was used for current measurement through the pressure and voltage applied nanopore. The sampling frequency was 250 kHz. The low pass filter cut off frequency was set to 5 kHz. A HumSilencer was enabled for noise cancellation. A pressure sensor that outputs a 0-5V signal was connected to the Digidata 1550 as an analog input for synchronous recording along with the current signals.

Nanoliposoine Synthesis

In glass vials, diphytanoyl phosphatidylcholine (DphPC), phosphatidylcholine (POPC), cholesterol, distearoyl-sn-glycero-3-phosphoethanolamine-Poly(ethylene glycol) (DSPE-PEG), and Texas-Red were added and covered with aluminum foil to prevent photobleaching. Afterwards, the glass vial was purged with $N_2$ for three minutes then placed in a vacuum chamber for 2-24 hours. Either $ddH_2O$ (unloaded) or drug solution (loaded, sodium salicylate) was added to the samples after vacuum. The samples were then left to incubate at room temperature for one hour. After incubation, samples were vortexed for three seconds at low speed. At this time, the samples were then placed in a sonicator bath for five minutes. Samples were secured to foam boards to keep from tipping over. During the sonication step, a hot plate was set to 25° C. and an extruder was placed on top of the plate. Also, filter supports were soaked in $ddH_2O$ during the sonication step. After sonication, copper wire was wrapped around each of the glass vials and the samples were dipped in liquid nitrogen for one minute. Samples were then placed under a stream of lukewarm water to make solution aqueous again. This process (freezing and melting) was repeated five times. To prepare for the extrusion process, the samples were then transferred to a beaker using a glass pipette. Filter supports (after soaking) were then placed into the extruder with one 100 nm membrane. Prior to extruding the samples, $ddH_2O$ was ran through to wet the filters and membrane. Once this was completed, the samples were extruded for a total of 16 pushes (8 forward and 8 backward) and the remaining solution was transferred into Eppendorf tubes for experimental usage.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method comprising:
    providing a fluid to a structure including an aperture, nanopipette, or nanopore;
    applying a voltage signal to a circuit that includes the fluid containing analyte;
    applying a substantially periodic pressure signal to the fluid; and
    detecting a current signal in the circuit as an analyte passes through the aperture in response to the substantially periodic pressure signal, wherein the substantially periodic pressure signal approximates a sine wave, square wave, or irregular wave having a peak positive pressure of about $10\times10^6$ pascals and a peak negative pressure of about minus $10\times10^6$ pascals.

2. The method of claim 1 wherein the analyte is a soft biological entity.

3. The method of claim 1, wherein applying the voltage signal to the circuit that includes the fluid comprises applying a substantially fixed voltage signal to the circuit.

4. The method of claim 1, wherein the substantially periodic pressure signal achieves a flow reversal of the fluid.

5. The method of claim 1, further comprising triggering a change in polarity of the pressure signal upon inward translocation of the analyte.

6. The method of claim 1, wherein the aperture has a diameter of 50-1000 nanometers and the analyte includes a red blood cell-derived nanoliposome.

7. The method of claim 5, wherein detecting a current signal in the circuit as an analyte passes through the aperture in response to the substantially periodic pressure signal comprises detecting the current signal in the circuit as a plurality of different biological species pass through the aperture.

8. The method of claim 1, wherein the fluid includes nanoliposomes or extracellular vesicles.

9. An apparatus comprising:
    a structure including an aperture (nanopipette or nanopore) to receive a fluid;
    a voltage source to provide a voltage signal to an electronic circuit having a path that includes the aperture;
    a pressure signal generator to provide a substantially periodic pressure signal to the fluid; the substantially periodic pressure signal approximates a sine wave, square wave, or irregular wave having a peak positive pressure of about $10\times10^6$ pascals and a peak negative pressure of about minus $10\times10^6$ pascals; and
    a system to process the periodic pressure signal and a current signal induced in the electronic circuit.

10. The apparatus of claim 9, wherein the structure includes a first chamber and a second chamber in fluid communication through the aperture.

11. The apparatus of claim 9, wherein the substantially periodic pressure signal includes a positive pressure signal and a negative pressure signal.

12. The apparatus of claim 10, wherein the aperture has a diameter of between about one-half micrometer and about three micrometers.

13. The apparatus of claim 9, where multiple parallel apertures (array of nano or micro pores) are used.

* * * * *